(12) United States Patent
Bell

(10) Patent No.: US 12,310,671 B2
(45) Date of Patent: May 27, 2025

(54) COMPUTER CONTROLLED SURGICAL ROTARY TOOL

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventor: Brett Bell, Mendon, UT (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 579 days.

(21) Appl. No.: 17/620,246

(22) PCT Filed: Jun. 18, 2020

(86) PCT No.: PCT/US2020/038414
§ 371 (c)(1),
(2) Date: Dec. 17, 2021

(87) PCT Pub. No.: WO2020/257444
PCT Pub. Date: Dec. 24, 2020

(65) Prior Publication Data
US 2022/0338935 A1 Oct. 27, 2022

Related U.S. Application Data

(60) Provisional application No. 62/863,039, filed on Jun. 18, 2019.

(51) Int. Cl.
*A61B 34/20* (2016.01)
*A61B 17/16* (2006.01)
*A61B 34/10* (2016.01)
*A61B 34/30* (2016.01)

(52) U.S. Cl.
CPC .............. *A61B 34/20* (2016.02); *A61B 17/16* (2013.01); *A61B 34/10* (2016.02); *A61B 34/30* (2016.02); *A61B 2034/2055* (2016.02)

(58) Field of Classification Search
CPC ......... A61B 34/20; A61B 34/10; A61B 34/30; A61B 2034/2055
See application file for complete search history.

(56) References Cited

U.S. PATENT DOCUMENTS

2013/0096574 A1* 4/2013 Kang ................. A61B 17/1622
606/130
2016/0113720 A1* 4/2016 Lavallee ................ A61B 17/15
901/9

FOREIGN PATENT DOCUMENTS

WO WO-2017091380 A1 * 6/2017 ........... A61B 17/154

* cited by examiner

*Primary Examiner* — Boniface N Nganga
(74) *Attorney, Agent, or Firm* — ArentFox Schiff LLP; Joseph M. Maraia

(57) ABSTRACT

A rotary tool includes a tool body and a powered rotary cutting tooltip that is oriented and positioned relative to the tool body by a plurality of processor-controlled actuators that provide degrees of freedom. The processor uses a surgical tracking system to identify the pose of the tool body and the tooltip relative to a patient's anatomy and controls the actuators to maintain the tooltip within a predetermined cutting plan to compensate for deviation of a surgeon's hand or a robotic arm controlling the tool body during a cutting operation.

20 Claims, 18 Drawing Sheets

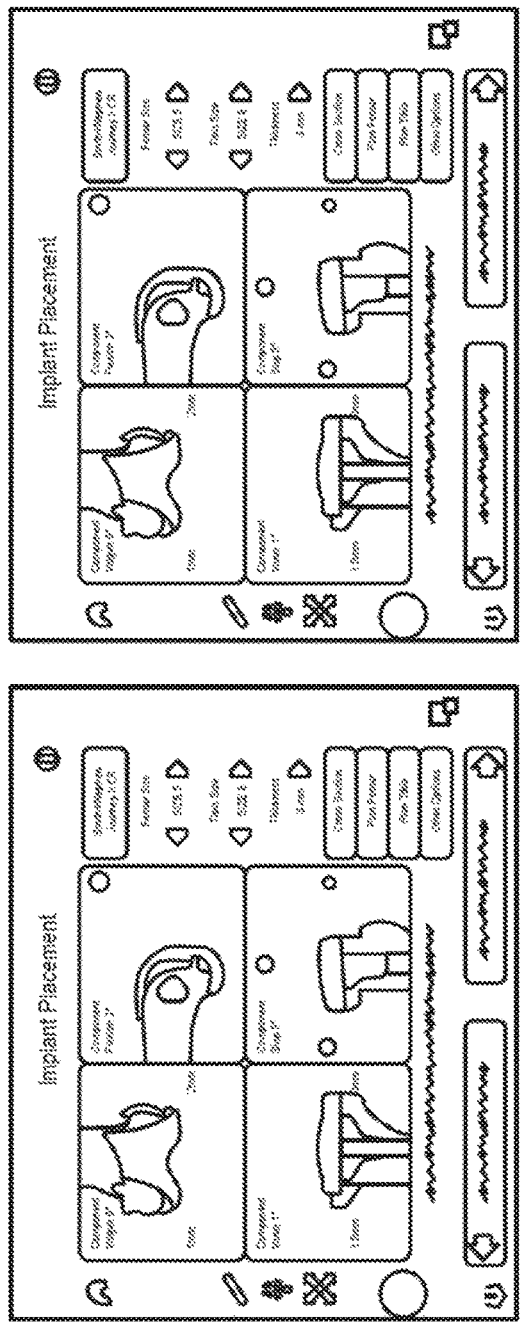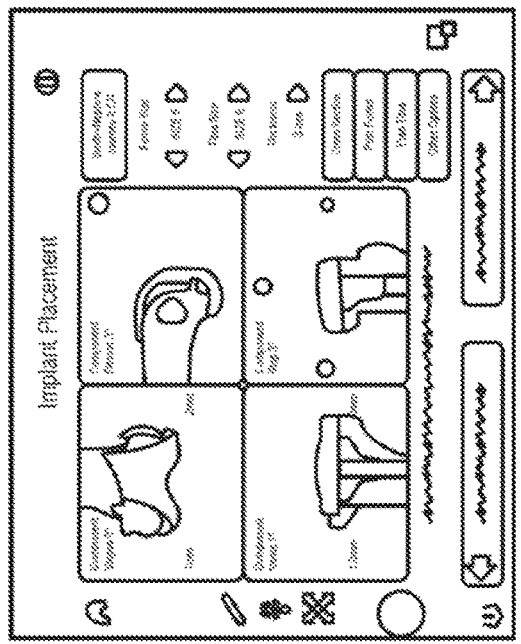
FIG. 7C

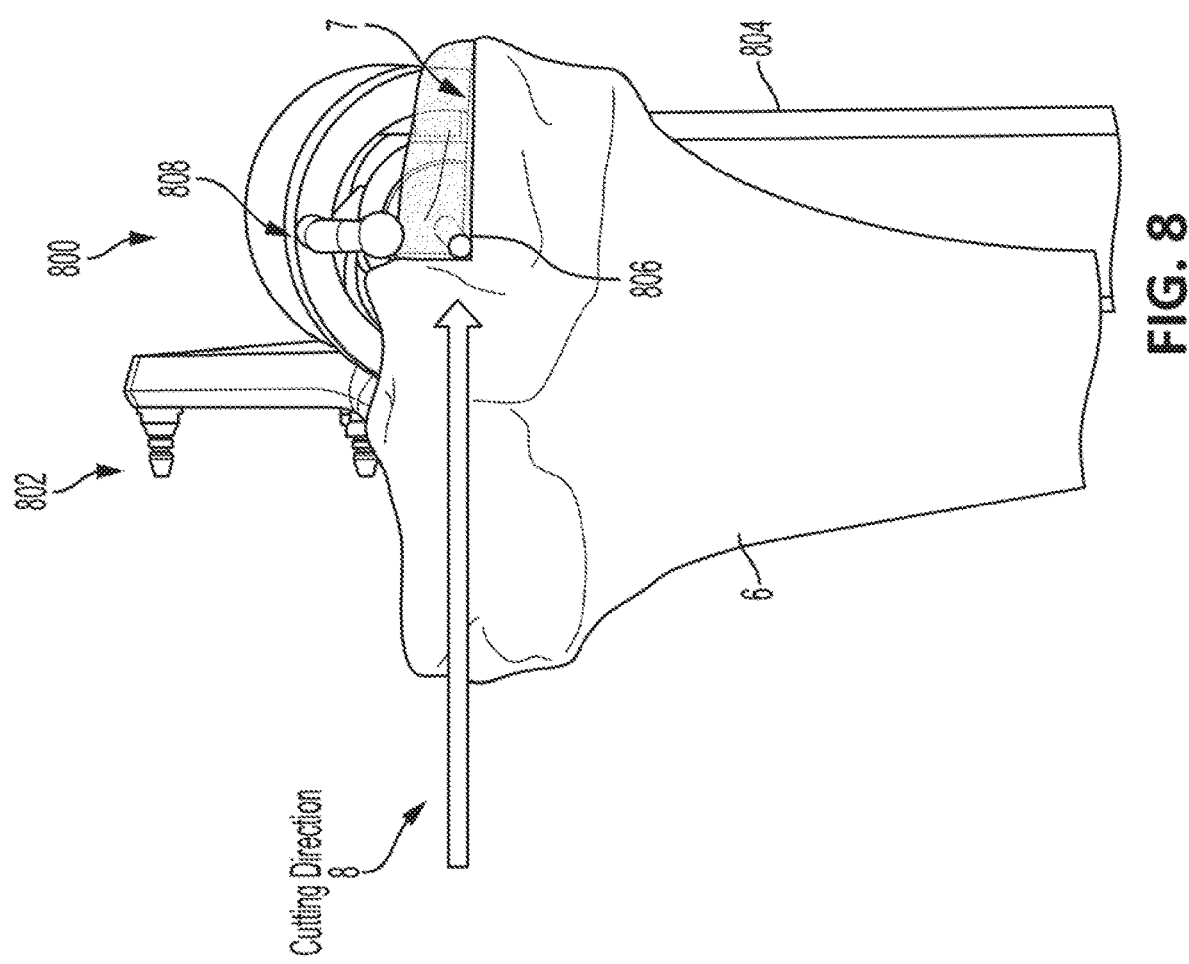

COMPUTER CONTROLLED SURGICAL ROTARY TOOL

CLAIM OF PRIORITY

This application is a U.S. National Stage filing under 35 U.S.C. § 371 of International PCT Application No. PCT/US2020/038414, filed Jun. 18, 2020, which claims the benefit of priority to U.S. Provisional Application No. 62/863,039, titled "Computer Controlled Surgical Rotary Tool," filed Jun. 18, 2019, each of which is incorporated herein by reference in its entirety.

TECHNICAL FIELD

The present disclosure relates generally to methods, systems, and apparatuses related to surgical rotary tool for resection bone in cooperation with a computer-assisted surgical system that includes various hardware and software components that work together to enhance surgical workflows and outcomes. More particularly, the present disclosure relates to a surgical rotary tool configured to be maintained with respect to a virtual cutting plane under the control of the computer-assisted surgical system. The disclosed techniques may be applied to, for example, shoulder, hip, and knee surgical procedures, as well as other surgical interventions such as arthroscopic procedures, spinal procedures, maxillofacial procedures, rotator cuff procedures, ligament repair and replacement procedures.

BACKGROUND

Conventional surgical operations have recently been enhanced through the use of robotic assistance. Robotic assistance can take on various degrees of enhancement to the traditional surgical process. Robotic enhancements can fully automate surgery or provide tracking and guidance to a surgeon beyond what may have traditionally been available. One type of system used to robotically enhance surgery is the NAVIO surgical system available from Smith and Nephew, Inc. NAVIO is a registered mark of Blue Belt Technologies, Inc., a wholly-owned subsidiary of Smith & Nephew.

Resection of bone for total knee replacement is commonly done using an oscillating saw and a cutting guide or jig. Postoperative function, pain, rehabilitation, and satisfaction can all be influenced by the placement of the implant. Robot assisted total knee arthroplasty (such as can be performed using the NAVIO system) seeks to improve accuracy and repeatability of implant placement. A disadvantage of some robotic surgical systems is the somewhat lengthy time required to resect the volume of bone necessary for a total knee replacement using the volumetric resection methods, such as a rotary burr.

In order to overcome the limitations of resection rates achievable with a burr, some systems utilize a hybrid approach where features of limited size are burred in specific/pre-planned locations using the robotic handpiece. Thereafter, a special cutting jig interfaces with the burred features in the bone which places the jigs into the correct position/orientation to resect bone using the traditional oscillating saw, allowing sections of bone to be cut off rather than ground down.

While this approach may be quicker than burring alone, it can have several limitations. For example, the features burred for cutting guides are "post holes" which are cumbersome for surgeons to create. Placement of cutting jigs into burred features can introduce additional error. Cutting with a saw can introduce yet more error. Some robotic systems utilize a robotic arm to directly constrain the saw to a resection plane. This can overcomes limitations of a system that mounts cutting guides using burred post holes. However, the complexity of the robotic arm can greatly increase cost.

The exemplary NAVIO surgical system assists surgeons by using optical tracking of tools in the surgical theater and tracking of patient anatomy relative to the tools. This tracking is typically performed by applying mechanical fiducial marks to the patient's anatomy (e.g., temporarily affixing fiducial markers to a patient's bone structure during arthroplasty and mounting fiducial markers to handpieces for tools). By using fiducial markers, objects within the surgical theatre can be optically tracked reliably and precisely. Once the objects in the surgical theatre are registered spatially with one another by the optical tracking system, any future movement of those objects can be tracked, and their motion can be captured and calculated via image processing and geometric modeling.

For example, once fiducial markers have been affixed to a patient's bones and have been registered with the system and a tool/handpiece also has been registered with the system, a surgeon can use that tool/handpiece to impinge the bone and register, via that impingement, the location of the salient features of the patient's bone structure. For example, during a knee replacement or corrective surgery, fiducial markers can be affixed to the femur and tibia. Using a probe with a tip at a predetermined location and orientation relative to fiducial markers attached to the probe, a surgeon can touch the tip of the probe to specific features on a tibial plateau and femoral condyles or to other important features for the surgical procedure. By tracking the location and orientation of the tibia and femur, via optical tracking of the fiducial markers, and by tracking the position and location of the probe (at the time of impingement of the bone to register those features of the tibia and femur), a three-dimensional model of the surgical theatre can be created via the robotic optical tracking system. Once the location of important features of the patient's bone structure have been identified and registered relative to fiducial markers, all future interaction with those bone features can be determined based on the location and the orientation of the tool relative to the fiducial markers on the bones.

SUMMARY

This summary is provided to comply with 37 C.F.R. § 1.73. It is submitted with the understanding that it will not be used to interpret or limit the scope or meaning of the present disclosure.

A system for resecting a bone of a patient is provided. The system comprises a rotary tool having a tool body, a tracking array affixed to the tool body, the tracking array comprising three or more fiducial markers, a powered rotary cutting tip comprising a longitudinal axis, wherein the rotary cutting tip is affixed to the tool body and rotatable about the longitudinal axis by a motor to resect the bone, first and second linear actuators configured to adjust one or more of a vertical position and a pitch position of the rotary cutting tip with respect to the tool body, and a tool rest extending from the tool body configured to maintain contact with the bone as the tool body is moved to resect the bone; a surgical tracking device configured to identify a position of each of the one or more fiducial markers with respect to the bone; and a processor configured to receive a surgical plan comprising at least one virtual cutting plane on the bone, receive a position of the tracking array from the surgical tracking device, determine, based on the position of the tracking array, a real-time pose of the cutting tip with respect to the at least one virtual cutting plane, and control the first and second linear actuators, based on the real-time pose, to adjust one or more of the vertical position and the pitch position of the rotary cutting tip with respect to the tool body in order to maintain the rotary cutting tip on the at least one virtual cutting plane.

According to some embodiments, the rotary cutting tip has a fixed horizontal position and a fixed axial position with respect to the tool body.

According to some embodiments, the rotary cutting tip has a fixed yaw position with respect to the tool body.

According to some embodiments, the processor is configured to prevent the rotary cutting tip from cutting across the at least one virtual cutting plane.

According to some embodiments, the at least one virtual cutting plane comprises a vertical cutting plane and a horizontal cutting plane. According to additional embodiments, the processor is further configured to maintain the longitudinal axis of the rotary cutting tip on the vertical cutting plane when a movement axis of the first and second linear actuators is substantially orthogonal to the vertical cutting plane; and maintain the longitudinal axis of the rotary cutting tip on the horizontal cutting plane when the movement axis of the first and second linear actuators is substantially orthogonal to the horizontal cutting plane. According to additional embodiments, the tool rest is further configured to pivot about a fixed point on a contact surface with the bone during movement of the rotary cutting tip along the vertical cutting plane; and move along the contact surface of the bone during movement of the rotary cutting tip along the horizontal cutting plane.

According to some embodiments, the processor is further configured to control a speed of rotation of the rotary cutting tip about the longitudinal axis to resect the bone. According to additional embodiments, the processor is further configured to stop rotation of the rotary cutting tip when the rotary cutting tip intersects the at least one virtual cutting plane. According to additional embodiments, the processor is further configured to stop rotation of the rotary cutting tip when the rotary cutting tip is moved outside of a prescribed cutting area.

According to some embodiments, each of the first and second linear actuators comprises one or more of a linear motor, a piezoelectric motor, a pneumatic motor, a hydraulic motor, and a gear motor.

According to some embodiments, the tool rest is rotatable with respect to the tool body.

According to some embodiments, the processor is further configured to control a position of a robotic arm to which the rotary tool is affixed.

A rotary tool for resecting a bone of a patient is provided. The rotary cutting tool comprises a tool body; a tracking array affixed to a tool body, the tracking array comprising one or more fiducial markers configured to be tracked by a surgical tracking system; a powered rotary cutting tip comprising a longitudinal axis, wherein the rotary cutting tip is affixed to the tool body and rotatable about the longitudinal axis by a motor to resect the bone of the patient; first and second linear actuators configured to be controlled by a processor to adjust one or more of a vertical position and a pitch position of the rotary cutting tip with respect to the tool body to maintain the rotary cutting tip on the at least one virtual cutting plane; and a tool rest extending from the tool body configured to maintain contact with the bone as the tool body is moved to resect the bone.

According to some embodiments, the rotary cutting tip has a fixed horizontal position and a fixed axial position with respect to the tool body.

According to some embodiments, the rotary cutting tip has a fixed yaw position with respect to the tool body.

According to some embodiments, each of the first and second linear actuators comprises one or more of a linear motor, a piezoelectric motor, a pneumatic motor, a hydraulic motor, and a gear motor.

According to some embodiments, the tool rest is rotatable with respect to the tool body.

According to some embodiments, the rotary tool is configured to be affixed to a robotic arm, wherein the processor is further configured to control a position of the robotic arm.

According to some embodiments, the tool rest is further configured to pivot about a fixed point on a contact surface with the bone during movement of the rotary cutting tip along a vertical cutting plane; and move along the contact surface of the bone during movement of the rotary cutting tip along a horizontal cutting plane.

BRIEF DESCRIPTION OF THE FIGURES

The accompanying drawings, which are incorporated in and form a part of the specification, illustrate the embodiments of the invention and together with the written description serve to explain the principles, characteristics, and features of the invention. In the drawings:

FIG. 7C depicts illustrative graphical user interfaces including images depicting an implant placement in accordance with an embodiment.

FIG. 8 is a side view of a cutting tool resecting a portion of a patient tibia, in accordance with some embodiments;

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon could also apply, in some embodiments to a technician or nurse.

CASS Ecosystem Overview

Figure 1:
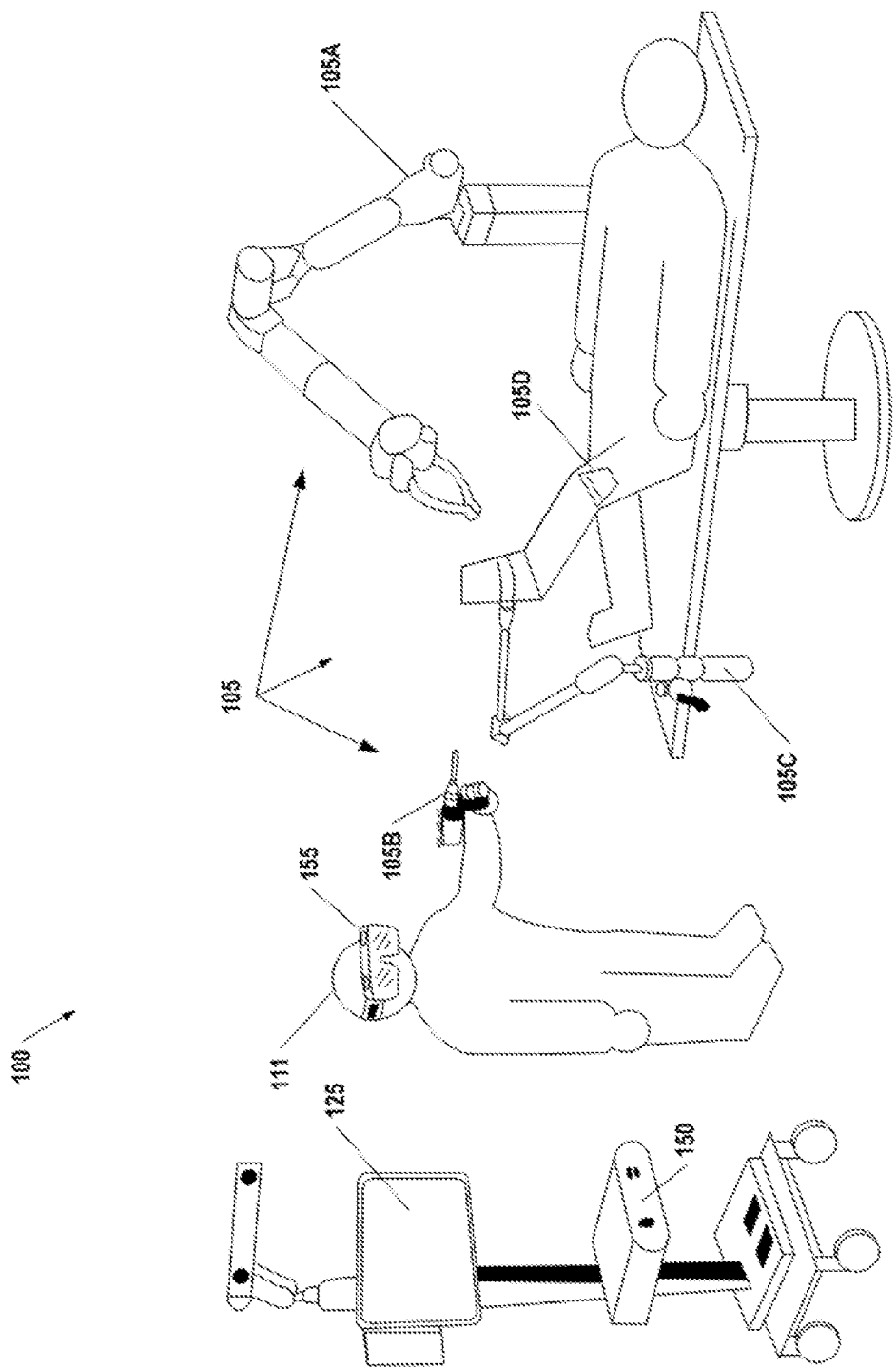
FIG. 1 depicts an operating theatre including an illustrative computer-assisted surgical system (CASS) in accordance with an embodiment.

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 can also include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 can also be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

Although, as discussed herein, the majority of tracking and/or navigation techniques utilize image-based tracking systems (e.g., IR tracking systems, video or image based tracking systems, etc.). However, electromagnetic (EM) based tracking systems are becoming more common for a variety of reasons. For example, implantation of standard optical trackers requires tissue resection (e.g., down to the cortex) as well as subsequent drilling and driving of cortical pins. Additionally, because optical trackers require a direct line of site with a tracking system, the placement of such trackers may need to be far from the surgical site to ensure they do not restrict the movement of a surgeon or medical professional.

Figure 2:
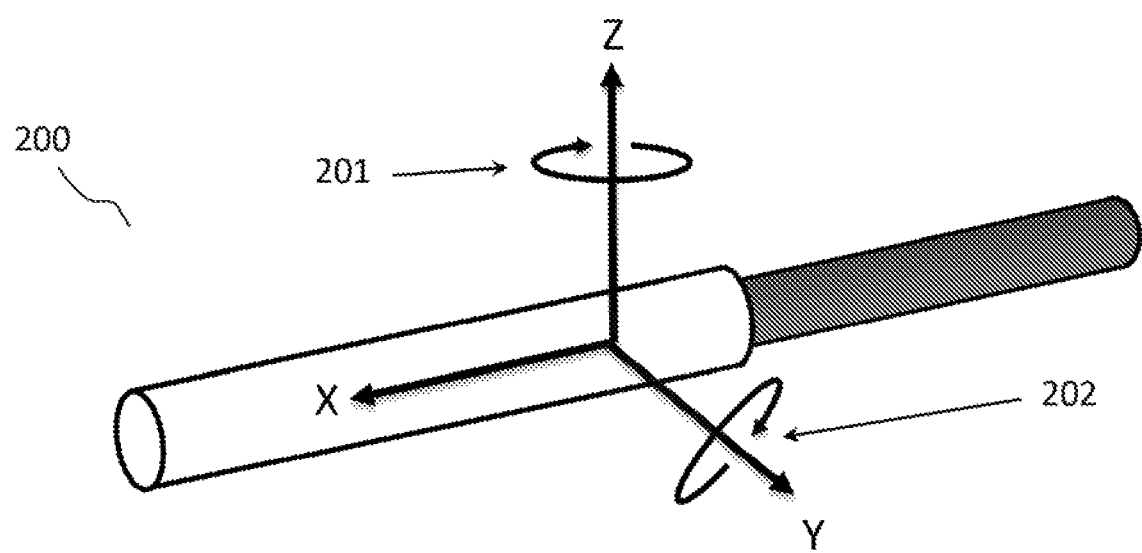
FIG. 2 depicts an example of an electromagnetic sensor device according to some embodiments.

Generally, EM based tracking devices include one or more wire coils and a reference field generator. The one or more wire coils may be energized (e.g., via a wired or wireless power supply). Once energized, the coil creates an electromagnetic field that can be detected and measured (e.g., by the reference field generator or an additional device) in a manner that allows for the location and orientation of the one or more wire coils to be determined. As should be understood by someone of ordinary skill in the art, a single coil, such as is shown in FIG. 2, is limited to detecting five (5) total degrees-of-freedom (DOF). For example, sensor 200 may be able to track/determine movement in the X, Y, or Z direction, as well as rotation around the Y-axis 202 or Z-axis 201. However, because of the electromagnetic properties of a coil, it is not possible to properly track rotational movement around the X axis.

Figure 3A:
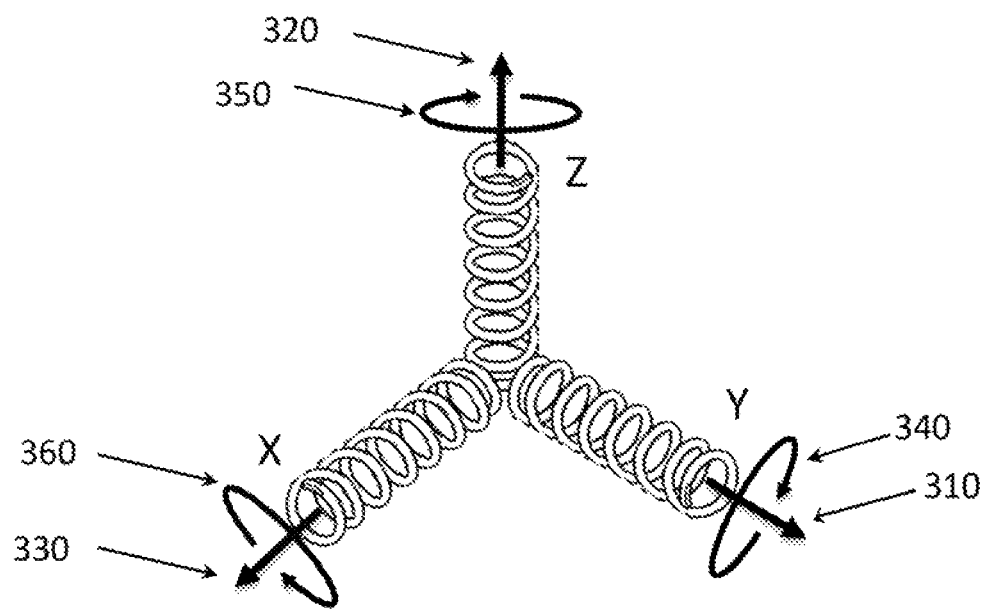
FIG. 3A depicts an alternative example of an electromagnetic sensor device, with three perpendicular coils, according to some embodiments.
Figure 3B:
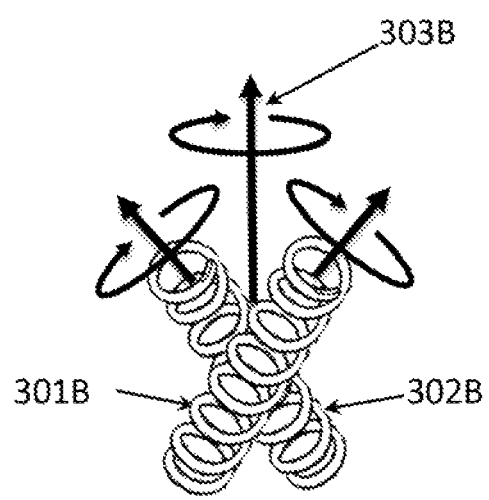
FIG. 3B depicts an alternative example of an electromagnetic sensor device, with two nonparallel, affixed coils, according to some embodiments.

Accordingly, in most electromagnetic tracking applications, a three coil system, such as that shown in FIG. 3A is used to enable tracking in all six degrees of freedom that are possible for a rigid body moving in a three-dimensional space (i.e., forward/backward 310, up/down 320, left/right 330, roll 340, pitch 350, and yaw 360). However, the inclusion of two additional coils and the 90° offset angles at which they are positioned may require the tracking device to be much larger. Alternatively, as one of skill in the art would know, less than three full coils may be used to track all 6DOF. In some EM based tracking devices, two coils may be affixed to each other, such as is shown in FIG. 3B. Because the two coils 301B and 302B are rigidly affixed to each other, not perfectly parallel, and have locations that are known relative to each other, it is possible to determine the sixth degree of freedom 303B with this arrangement.

Although the use of two affixed coils (e.g., 301B and 302B) allows for EM based tracking in 6DOF, the sensor device is substantially larger in diameter than a single coil because of the additional coil. Thus, the practical application of using an EM based tracking system in a surgical environment may require tissue resection and drilling of a portion of the patient bone to allow for insertion of a EM tracker. Alternatively, in some embodiments, it may be possible to implant/insert a single coil, or 5DOF EM tracking device, into a patient bone using only a pin (e.g., without the need to drill or carve out substantial bone).

Figure 3C:
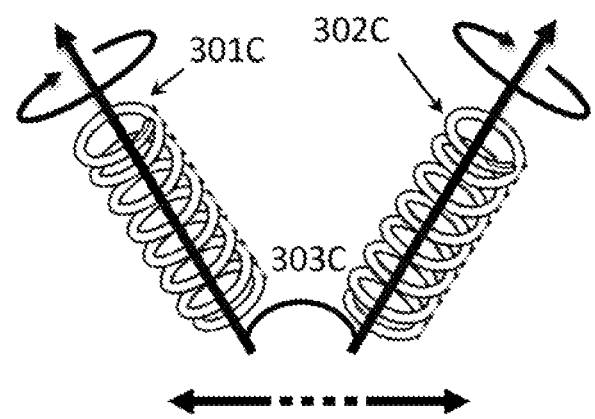
FIG. 3C depicts an alternative example of an electromagnetic sensor device, with two nonparallel, separate coils, according to some embodiments.

Thus, as described herein, a solution is needed for which the use of an EM tracking system can be restricted to devices small enough to be inserted/embedded using a small diameter needle or pin (i.e., without the need to create a new incision or large diameter opening in the bone). Accordingly, in some embodiments, a second 5DOF sensor, which is not attached to the first, and thus has a small diameter, may be used to track all 6DOF. Referring now to FIG. 3C, in some embodiments, two 5DOF EM sensors (e.g., 301C and 302C) may be inserted into the patient (e.g., in a patient bone) at different locations and with different angular orientations (e.g., angle 303C is non-zero).

Figure 4:
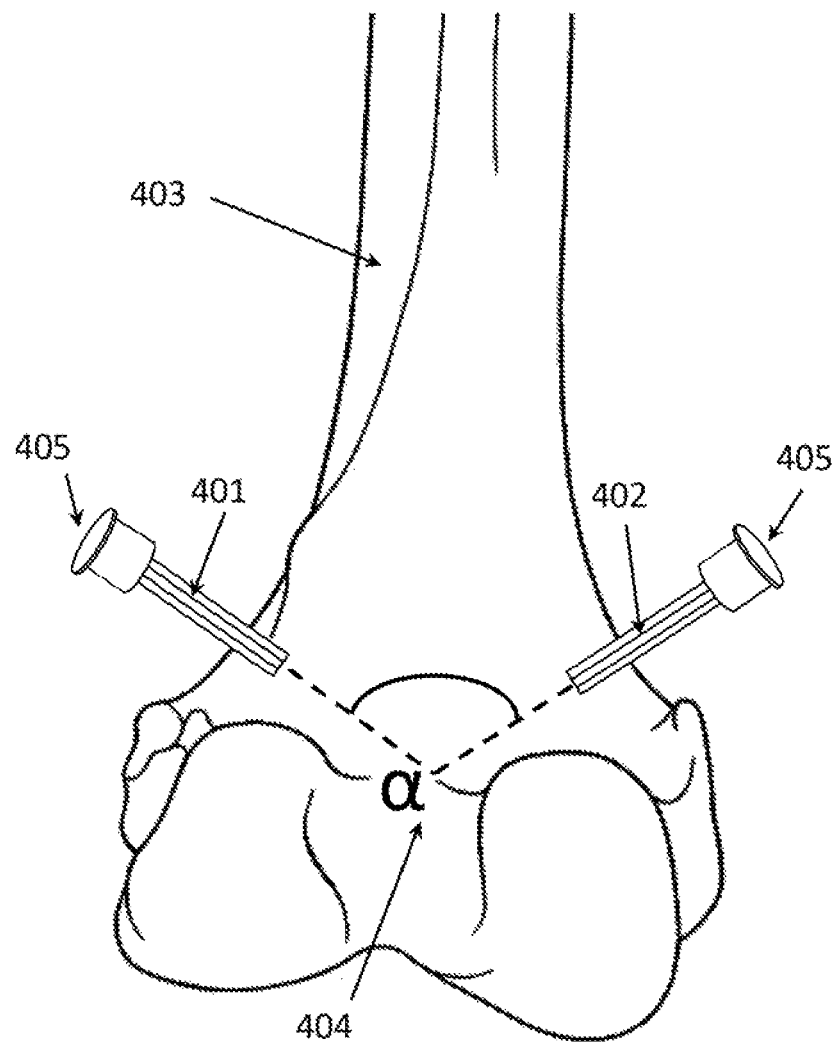
FIG. 4 depicts an example of electromagnetic sensor devices and a patient bone according to some embodiments

Referring now to FIG. 4, an example embodiment is shown in which a first 5DOF EM sensor 401 and a second 5DOF EM sensor 402 are inserted into the patient bone 403 using a standard hollow needle 405 that is typical in most OR(s). In a further embodiment, the first sensor 401 and the second sensor 402 may have an angle offset of "?" 404. In some embodiments, it may be necessary for the offset angle "?" 404 to be greater than a predetermined value (e.g., a minimum angle of 0.50°, 0.75°, etc.). This minimum value may, in some embodiments, be determined by the CASS and provided to the surgeon or medical professional during the surgical plan. In some embodiments, a minimum value may be based on one or more factors, such as, for example, the orientation accuracy of the tracking system, a distance between the first and second EM sensors. The location of the field generator, a location of the field detector, a type of EM sensor, a quality of the EM sensor, patient anatomy, and the like.

Accordingly, as discussed herein, in some embodiments, a pin/needle (e.g., a cannulated mounting needle, etc.) may be used to insert one or more EM sensors. Generally, the pin/needle would be a disposable component, while the sensors themselves may be reusable. However, it should be understood that this is only one potential system, and that various other systems may be used in which the pin/needle and/or EM sensors are independently disposable or reusable. In a further embodiment, the EM sensors may be affixed to the mounting needle/pin (e.g., using a luer-lock fitting or the like), which can allow for quick assembly and disassembly. In additional embodiments, the EM sensors may utilize an alternative sleeve and/or anchor system that allows for minimally invasive placement of the sensors.

In another embodiment, the above systems may allow for a multi-sensor navigation system that can detect and correct for field distortions that plague electromagnetic tracking systems. It should be understood that field distortions may result from movement of any ferromagnetic materials within the reference field. Thus, as one of ordinary skill in the art would know, a typical OR has a large number of devices (e.g., an operating table, LCD displays, lighting equipment, imaging systems, surgical instruments, etc.) that may cause interference. Furthermore, field distortions are notoriously difficult to detect. The use of multiple EM sensors enables the system to detect field distortions accurately, and/or to warn a user that the current position measurements may not be accurate. Because the sensors are rigidly fixed to the bony anatomy (e.g., via the pin/needle), relative measurement of sensor positions (X, Y, Z) may be used to detect field distortions. By way of non-limiting example, in some embodiments, after the EM sensors are fixed to the bone, the relative distance between the two sensors is known and should remain constant. Thus, any change in this distance could indicate the presence of a field distortion.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient can also involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process can also include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 can also utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step can also utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon. In some embodiments, the powered impactor device may have a dual function. For example, the powered impactor device not only could provide reciprocating motion to provide an impact force, but also could provide reciprocating motion for a broach or rasp.

In some embodiments, the powered impaction device includes feedback sensors that gather data during instrument use, and send data to a computing device such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 can also place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in U.S. Provisional Patent Application No. 62/723,898 filed Aug. 28, 2018 and entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various aspects of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 5C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 5A:
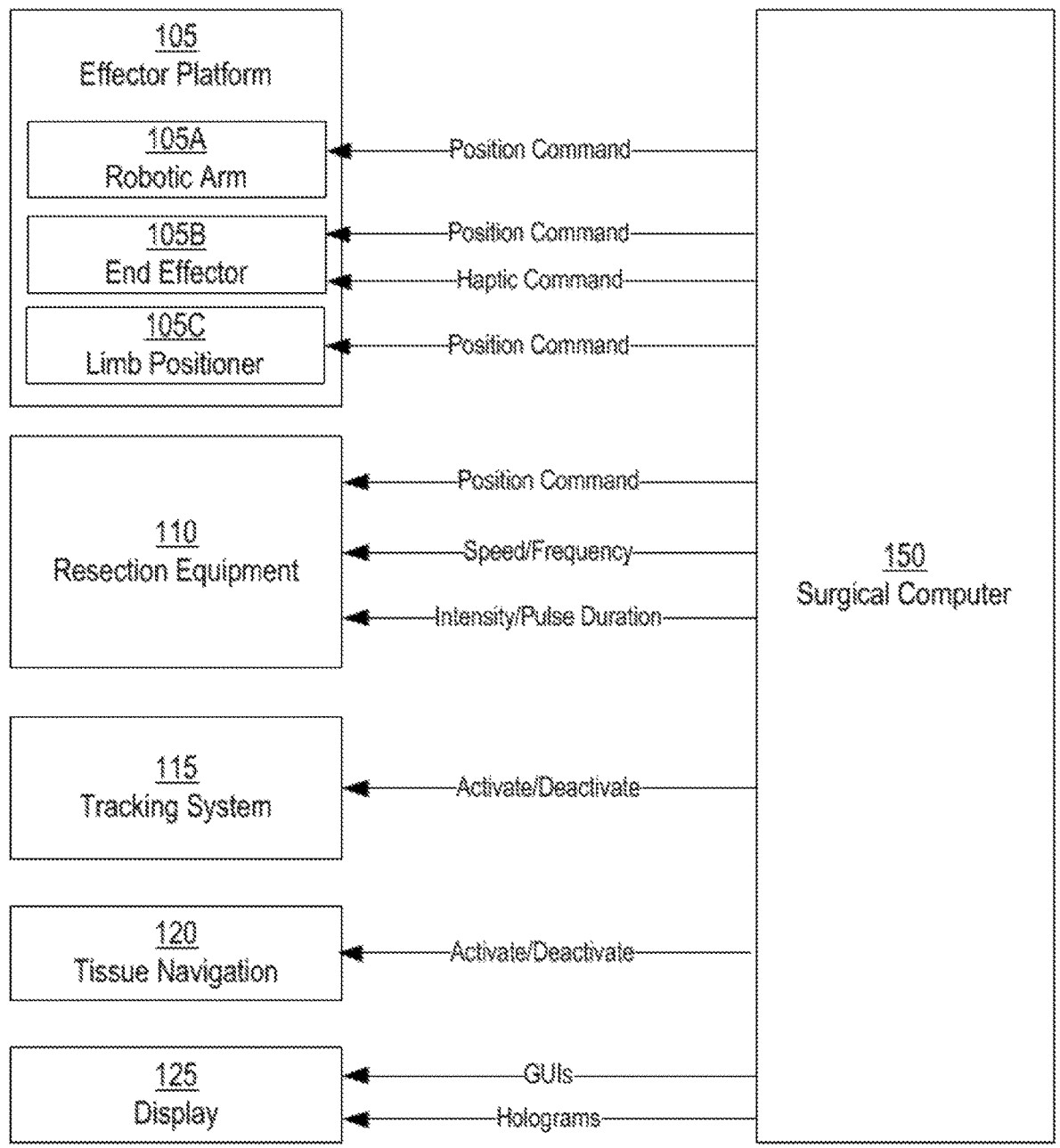
FIG. 5A depicts illustrative control instructions that a surgical computer provides to other components of a CASS in accordance with an embodiment.
Figure 5B:
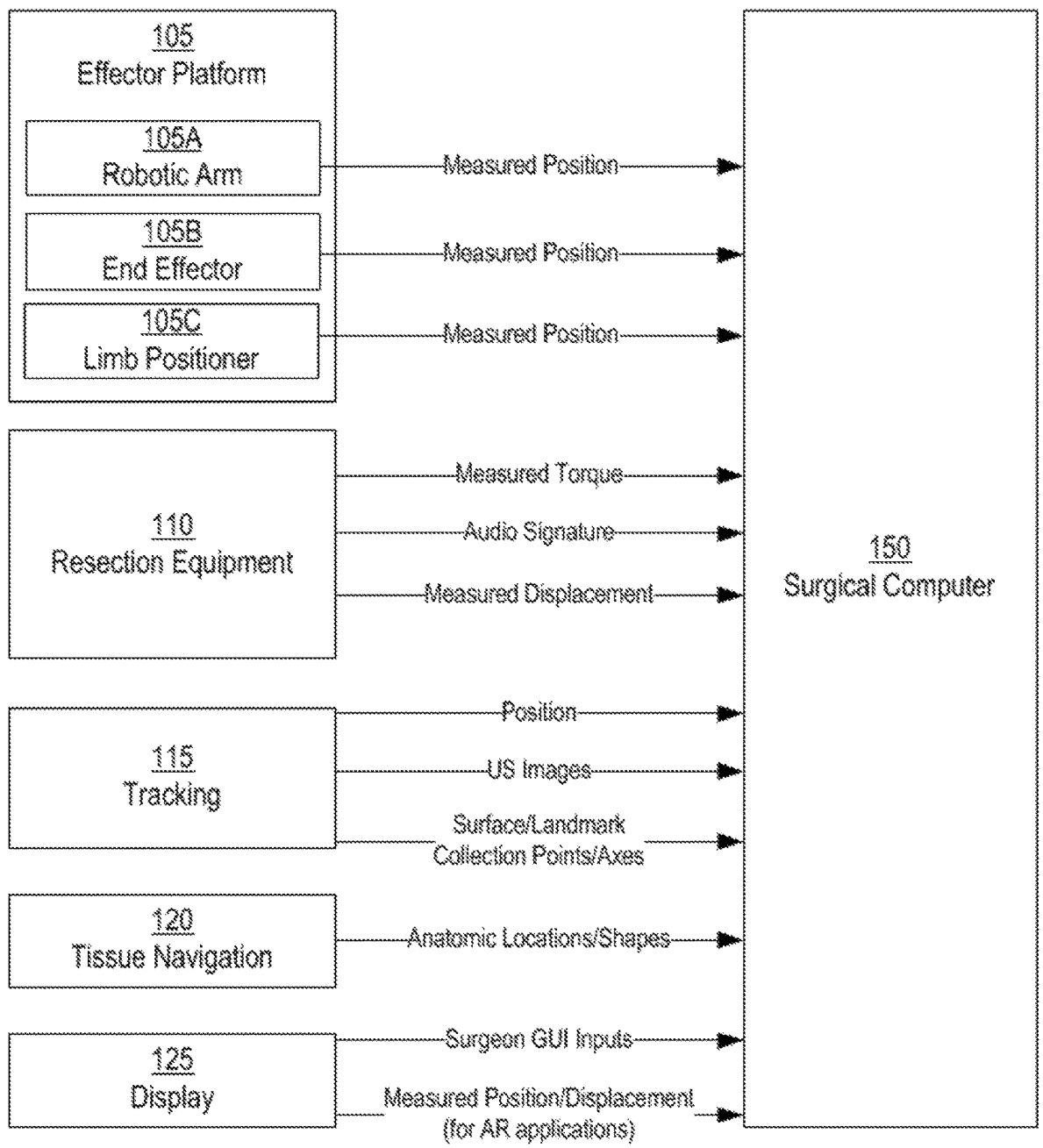
FIG. 5B depicts illustrative control instructions that components of a CASS provide to a surgical computer in accordance with an embodiment.

FIGS. 5A and 5B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 5A shows examples of some of the control instructions that the Surgical Computer 150 provides to other components of the CASS 100, according to some embodiments. Note that the example of FIG. 5A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 5A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 5A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various aspects of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 can also include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 can also provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 can also preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 5C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in U.S. Provisional Patent Application No. 62/719,415 entitled "Patient Specific Surgical Method and System," the entirety of which is incorporated herein by reference.

FIG. 5B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 5B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQ5D-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 5C.

Figure 5C:
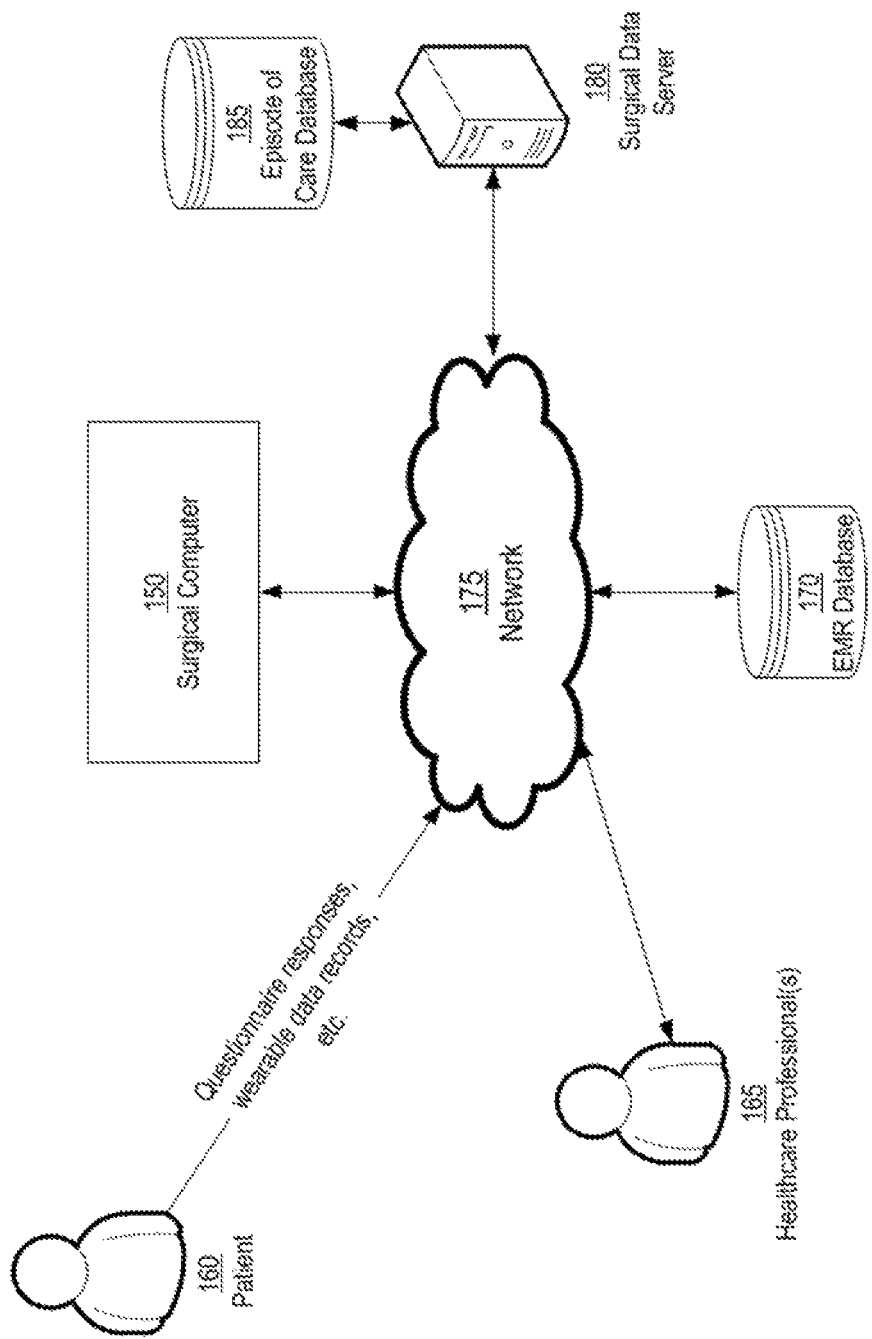
FIG. 5C depicts an illustrative implementation in which a surgical computer is connected to a surgical data server via a network in accordance with an embodiment.

FIG. 5C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 5C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 5C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 5A-5C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation(s) |
|---|---|---|
| Size | Posterior | The largest sized implant that does not overhang medial/lateral bone edges or overhang the anterior femur. A size that does not result in overstuffing the patella femoral joint |
| Implant Position - Medial Lateral | Medial/lateral cortical bone edges | Center the implant evenly between the medial/lateral cortical bone edges |
| Resection Depth - Varus Knee | Distal and posterior lateral | 6 mm of bone |
| Resection Depth - Valgus Knee | Distal and posterior medial | 7 mm of bone |
| Rotation - Varus/Valgus | Mechanical Axis | 1° varus |
| Rotation - External | Transepicondylar Axis | 1° external from the transepicondylar axis |
| Rotation - Flexion | Mechanical Axis | 3° flexed |

Additional examples of parameters that could be optimized for a given TKA tibial implant by the CASS 100 include the following:

| Parameter | Reference | Exemplary Recommendation(s) |
|---|---|---|
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth - Varus Knee | Lateral/Medial | 4 mm of bone |
| Resection Depth - Valgus Knee | Lateral/Medial | 5 mm of bone |
| Rotation - Varus/Valgus | Mechanical Axis | 1° valgus |
| Rotation - External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 6:
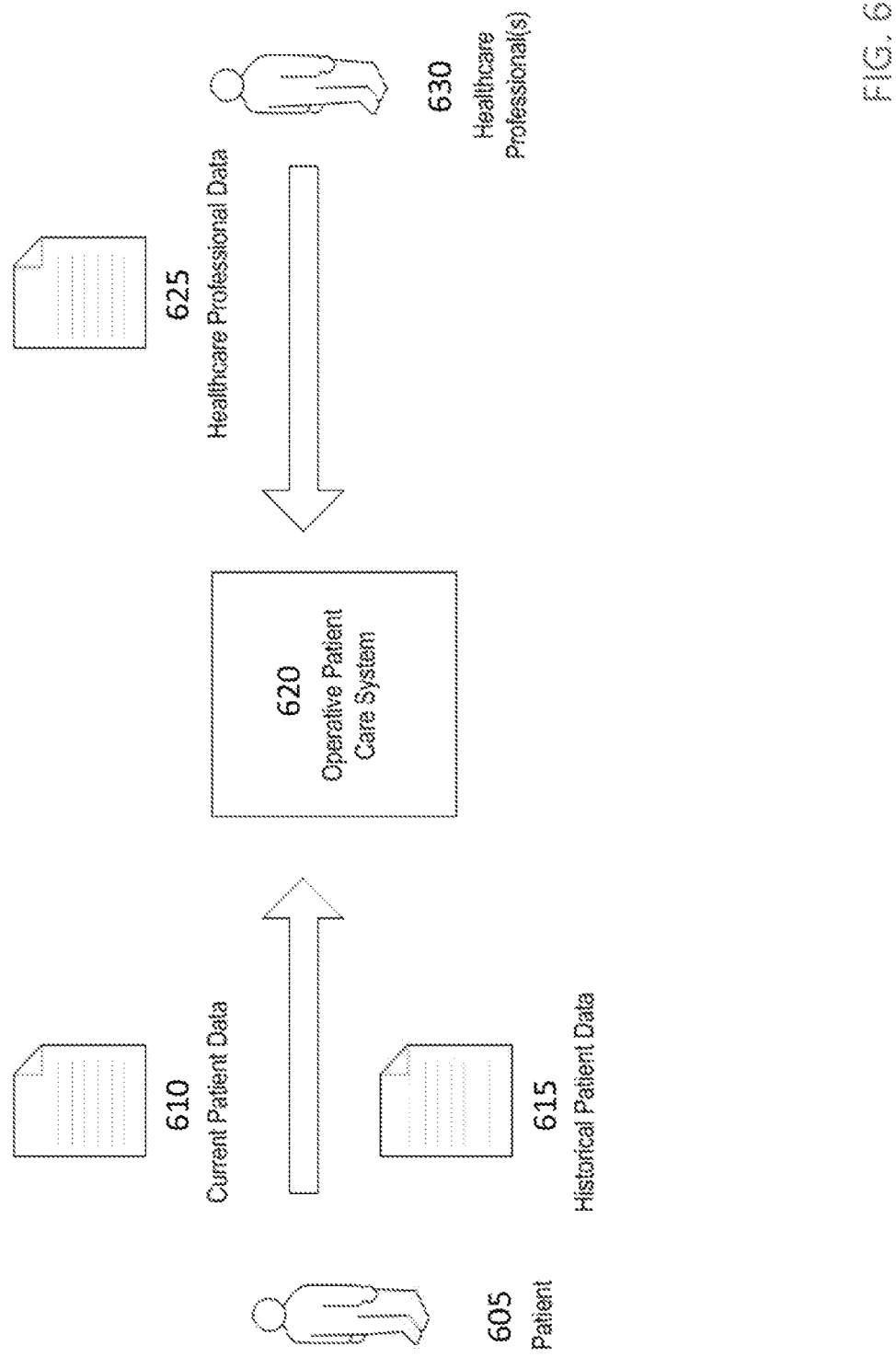
FIG. 6 depicts an operative patient care system and illustrative data sources in accordance with an embodiment.

The general concepts of optimization may be extended to the entire episode of care using an Operative Patient Care System 620 that uses the surgical data, and other data from the Patient 605 and Healthcare Professionals 630 to optimize outcomes and patient satisfaction as depicted in FIG. 6.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 620 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 620 tracks adherence to the suggested or recommended plan, and adapts the plan based on patient/care provider performance. Once the surgical treatment plan is complete, collected data is logged by the Operative Patient Care System 620 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 620 ensures that each patient is receiving personalized surgical and rehabilitative care, thereby improving the chance of successful clinical outcomes and lessening the economic burden on the facility associated with near-term revision.

In some embodiments, the Operative Patient Care System 620 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 605 provides inputs such as Current Patient Data 310 and Historical Patient Data 615 to the Operative Patient Care System 620. Various methods generally known in the art may be used to gather such inputs from the Patient 605. For example, in some embodiments, the Patient 605 fills out a paper or digital survey that is parsed by the Operative Patient Care System 620 to extract patient data. In other embodiments, the Operative Patient Care System 620 may extract patient data from existing information sources, such as electronic medical records (EMRs), health history files, and payer/provider historical files. In still other embodiments, the Operative Patient Care System 620 may provide an application program interface (API) that allows the external data source to push data to the Operative Patient Care System. For example, the Patient 605 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 620. Similarly, the Patient 605 may have a digital application on his or her mobile or wearable device that enables data to be collected and transmitted to the Operative Patient Care System 620.

Current Patient Data 610 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 615 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 630 conducting the procedure or treatment may provide various types of data 625 to the Operative Patient Care System 620. This Healthcare Professional Data 625 may include, for example, a description of a known or preferred surgical technique (e.g., Cruciate Retaining (CR) vs Posterior Stabilized (PS), up-vs down-sizing, tourniquet vs tourniquet-less, femoral stem style, preferred approach for THA, etc.), the level of training of the Healthcare Professional(s) 630 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 625 can be captured, for example, with paper or digital surveys provided to the Healthcare Professional 630, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socio-economic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFEMOD®, AnyBody, or OpenSIM). It is noted that the data inputs described above may not be available for every patient, and the treatment plan will be generated using the data that is available.

Prior to surgery, the Patient Data 610, 615 and Healthcare Professional Data 625 may be captured and stored in a cloud-based or online database (e.g., the Surgical Data Server 180 shown in FIG. 5C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 7A:
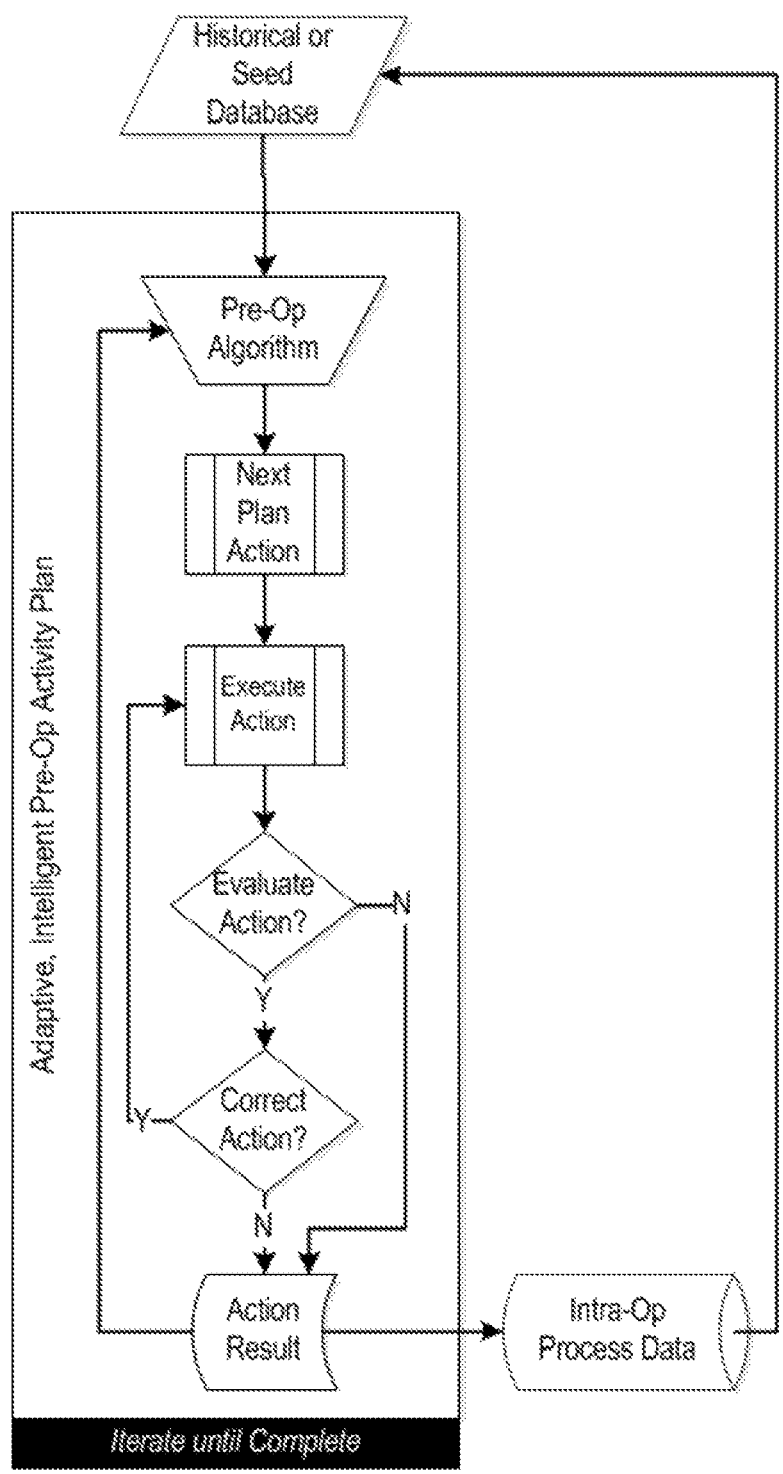
FIG. 7A depicts an illustrative flow diagram for determining a pre-operative surgical plan in accordance with an embodiment.
Figure 7B:
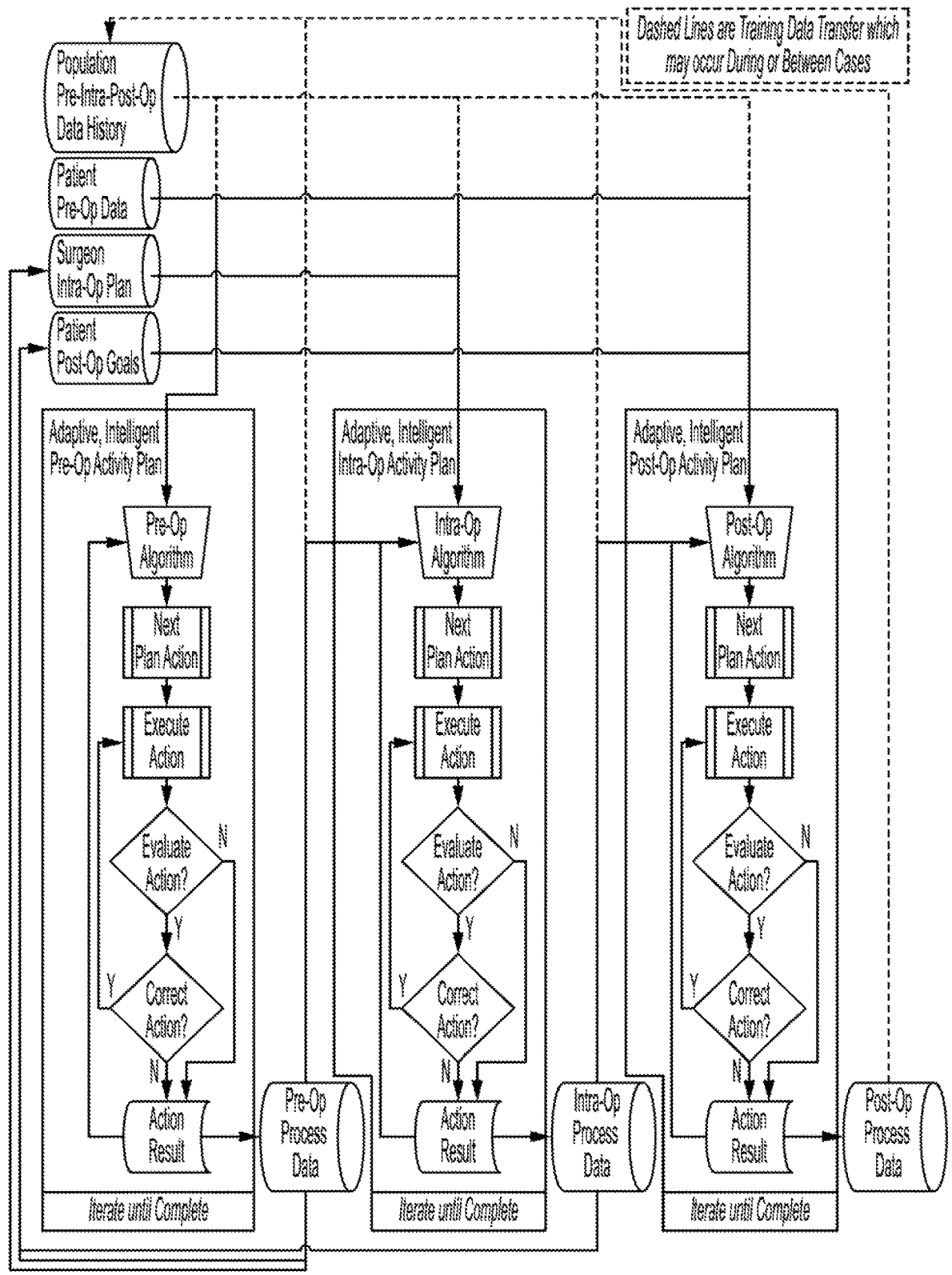
FIG. 7B depicts an illustrative flow diagram for determining an episode of care including pre-operative, intraoperative, and post-operative actions in accordance with an embodiment.

FIG. 7A illustrates how the Operative Patient Care System 620 may be adapted for performing case plan matching services. In this example, data is captured relating to the current patient 610 and is compared to all or portions of a historical database of patient data and associated outcomes 615. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular aspect of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 7B and can be applied to any type of surgery utilizing the CASS 100.

Surgery Process Display

As noted above with respect to FIGS. 1 and 5A-5C, the various components of the CASS 100 generate detailed data records during surgery. The CASS 100 can track and record various actions and activities of the surgeon during each step of the surgery and compare actual activity to the preoperative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different aspects of the actual surgery vs. the surgical plan could provide benefits to the surgeon and/or surgical staff, allowing such persons to identify any deficiencies or challenging aspects of a surgery so that they can be modified in future surgeries. Similarly, in academic settings, the aforementioned GUIs can be used as a teaching tool for training future surgeons and/or surgical staff. Additionally, because the data set effectively records many aspects of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, aspects such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 7C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other aspects of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various aspects of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. Provisional Patent Application No. 62/658,988, filed Apr. 17, 2018 and entitled "Three Dimensional Guide with Selective Bone Matching," the entirety of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Don Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data could also be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light inferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

As described herein, some embodiments of the present disclosure are particularly well adapted for surgical procedures that utilize surgical navigation systems, such as the NAVIO surgical navigation system, that use optical tracking of patient anatomy and tools in the surgical theatre. Such procedures can include knee replacement and/or revision surgery, as well as shoulder and hip surgeries.

Some embodiments of the present disclosure are well-suited for use with handheld surgical tools that have a position and orientation (which can be called a pose) that is tracked and modeled relative to sensors (e.g., optical sensors, cameras, position encoders, RF/microwave/laser distance measurement, etc.) Such tools can be adapted to be held by a surgeon's hand or by a robotic arm, in various embodiments. In some embodiments that utilize a robotic arm to hold the tool, position and orientation of the tool can be determined from sensors, such as position encoders, that detect the real-time geometry of the robotic arm. As used herein, the term tool or handpiece can refer to a tool that can be held by surgeon or to a tool that can be held or mounted to or integrated with a robotic arm. While many embodiments may provide the most benefit to handheld tools, embodiments are not intended to be limited to handheld tools unless noted.

Embodiments of the invention utilize a tool with at least two degrees of freedom for manipulating a tool tip relative to a tool body, where these degrees of freedom are controlled by a processor of a surgical system. In some embodiments, the tool is a handheld (or robotically held) device with fiducial marks to allow optical tracking of the position and orientation of the tool body relative to patient anatomy. In some embodiments, other conventional sensor means can be used to track position and orientation. By tracking the position of the tool body relative to patient anatomy, a processor can control the position of the tooltip relative to the tool body, and by extension relative to patient anatomy, to provide processor control of the tooltip. This can allow smoother, refined cutting with a tooltip, even when the tool body is used in a freehand manner or by a robotic arm that lacks precise control. The processor can track the tool body and adjust the degrees of freedom to adjust to the position of the cutting tip relative to the patient anatomy based on the position and orientation of the handheld device.

By utilizing processor control of the tooltip relative to the tool body, a processor can define a cutting plane. The plane can be identified in a surgical plan based on preoperative imaging or intraoperative measurements. The plane can be selected based on an implant geometry for a knee or hip partial or total arthroplasty. In embodiments that utilize two degrees of freedom, an axis of the tool tip can be defined with an offset position and orientation in one dimension. If a tool body is held in roughly the same vertical or horizontal orientation (with a slow drift of up to several degrees, such as +/−40 degrees in some embodiments) during a cut, two degrees of freedom are sufficient to approximately maintain the tooltip in a cutting plane. This allows a surgeon or robotic arm to hold the tool and move it generally in the direction of the cutting plane while a processor provides real-time control to maintain the tooltip in the desired cutting plane with precision, providing a smoother, straighter/flatter, and more consistent cut than could be achieved with a freehand cut. This planar cut will generally be sufficient to directly interface with an implant with minimal post-cut surface preparation.

In addition to using two degrees of freedom to maintain the cutting tip in line with a predetermined cutting plane, processor control of the rotational speed of the cutting tip can be used to allow the processor to control the extent of the cut in that cutting plane. For example, as an operator moves the cutting tip along the cutting plane near the edge of the prescribed cut (according to the surgical plan) the processor can slow down the tip rotational speed to give finer control as the operator approaches the edge of the cut. Similarly, the processor can stop the rotation of the tip as the operator moves to the predetermined end of the cut. The terminal edges of the cut in the cutting plane can be thought of as the intersection of two generally orthogonal planes.

An exemplary tool for use with embodiments is a rotary cutting tool that cuts perpendicular to the axis of an elongated cutting tooltip. This rotary cutting tool can be a surgical burr or a linear, sharpened fluted cutting bit, such as a helically cut milling bit. This allows several millimeters or more of cutting length along the axis of the cutting/burring tooltip. A fluted cutting bit can give a smooth cut when the cutting bit is maintained in a predetermined cutting plane. The entire cutting surface can be considered the cutting tip, and the processor seeks to control the position of this cutting surface to ensure it stays within a predetermined cutting plane. Two or more degrees of freedom can be used to adjust the position of the axis of the cutting tool relative to an axis of the tool body and the angle between these two axes. More than two degrees of freedom can allow control of other positional offsets (e.g. in lateral or transverse directions) as well as the angle between the axis of the tooltip and other axes of the tool body (e.g. a lateral or transverse axis). It will be appreciated that the number of degrees of freedom can be chosen to balance complexity and cost with precision and control of the position and the orientation of the tooltip relative to the tool body.

In the example where two degrees of freedom are used, these degrees may be presented as linear extension or contraction devices (actuators) running parallel to an axis of the tool body and roughly perpendicular to the axis of the tooltip. These actuators can be coupled between points in the tool body and points on a motor carriage/housing that maintains the angle of the tool tip and provides rotational force on demand. By extending or contracting these devices along the tool body axis, the position of the axis of the tooltip along the axis of the tool body as well as of the angle between these two axes can be manipulated under processor control. This allows the axis of the tooltip to be manipulated to always lie along a virtual cutting plane whenever the axis of the tool body is roughly aligned (within several degrees) with the normal axis of the plane. The operator can deviate from this normal axis by several degrees in any direction and the manipulation of the degrees of freedom can counteract the difference between the tool body axis and the normal axis of the plane. When using only two degrees of freedom, it should be noted, that the tooltip axis may not always be maintained in the same orientation within that plane, but the tool tip can be maintained in a direction that is parallel to the two-dimensional plane. For a planar cut, the tool orientation within that plane is generally unimportant to maintaining a smooth, flat cut with a rotary tool, except near boundaries. Thus, real-time control of the offset and orientation of the tooltip relative to the axis of the tool body can compensate for any deviations in the position and orientation of the tool body relative to the virtual cutting plane, within several degrees of deviation. This can allow aberrant motion of a surgeon's hand or robotic arm without compromising the ability of the tooltip to cut along the virtual cut plane with a smooth and straight cut, provided any aberrant motion of the tool body is not faster than the processor and actuators can compensate for the deviation. The processor can use any suitable control method, such as a proportional-integral-derivative controller (PID), or a machine learning algorithm to predict motion and compensate for it, to manipulate the tooltip to provide a suitably smooth and accurate cut.

FIG. 8 shows an exemplary cutting tool 800 for resecting a portion 7 of a patient bone 6. After a vertical cut, the tool 800 resects the bone 6 along a plane in a cutting direction 8. The tool 800 includes a fiducial marker array 802 affixed to a tool body 804 that facilitates optical tracking of the position and location of the tool body. A rotary cutting tooltip 806 cuts perpendicular to its axis as it moves along the cutting direction 8. Internal actuators provide degrees of freedom to move the position and vertical orientation of the cutting tooltip 806 relative to the tool body 804.

In some embodiments, the tooltip 806 extends from the tool body 804 at a depth that is less than the total depth of the patient bone 6. In such embodiments, upon completion of the cut in the cutting direction 8, the resected portion 7 will need to be further removed, but the resected surface will be flat and smooth. Other surgical tools, such as rasps or osteotomes may be used to complete the resection and flatten any portion of the patient bone 6 that was not cut by the tooltip 806.

In some embodiments, a diameter of the tooltip 806 varies along the length of the tooltip. For example, the tooltip 806 may be tapered distally such that a distal portion of the tooltip 806 has a smaller diameter than a proximal portion of the tooltip 806. The diameters at various portions of the tooltip 806 may be selected to control the stiffness and/or required motor torque for cutting and removing bone. For example, a greater diameter at portions of the tooltip 806 may provide greater stiffness to the tooltip 806 and a smaller diameter at portions of the tooltip 806 may reduce the necessary motor torque to rotate the tooltip 806 and/or the necessary force applied by the surgeon to cut through bone. Accordingly, in some embodiments, diameters at each portion of the tooltip 806 and/or a slope of a tapered portion of the tooltip 806 may be selected to provide an optimal balance of stiffness and required motor torque for the tooltip 806. In additional embodiments, the diameter of the tooltip 806 is constant along the length of the tooltip 806 and the diameter may be selected to provide an optimal balance of stiffness and motor torque for the tooltip 806.

In some embodiments, a tool rest or cutting guide 808 is provided as part of the tool body 804. This cutting guide 808 allows the tool body 804 to be in mechanical contact with a surface of the patient bone 6 during the cutting operation. As such, the cutting guide 808 can be used to reduce vibration and deviation from the cutting plane. Furthermore, a processor can determine a rough model of the path that the tooltip 806 will follow relative to the tool body 804 as the tool is moved in the cutting direction 8 because the necessary distance between the tooltip 806 and the cutting guide 808 is largely dictated by the geometry of the cutting plane relative to the surface of the patient bone 6 and any angular deviation introduced by the robotic arm or surgeon's hand. The offset distance between the tooltip 806 and the cutting guide 808 may be predetermined and/or input to the processor. Accordingly, the processor may predict the path of the tooltip 806 and plan actuation of tooltip to maintain the tooltip at the cutting plane. For example, a model of the patient bone 6 may be utilized to identify changes in height (e.g., a peak or a valley) along the upper surface of the patient bone 6. Because the cutting guide 808 slides along the upper surface of the patient bone 6, the processor may use this information to predict corresponding changes in the vertical position of the tool 800 and begin to adjust the position of the tooltip 806 in a predictive manner. For example, the processor may begin to adjust the position of the tooltip 806 before movement of the tool body 804 is detected by a tracking system. The processor may also utilize a speed and/or vector of movement of the tool 800 along the cutting plane to predict the timing of the adjustments to the position of the tooltip 806. The predictive control of the tooltip 806 as described herein may additionally compensate for lag or gaps in detection of the position of the tool 800.

Figure 9:
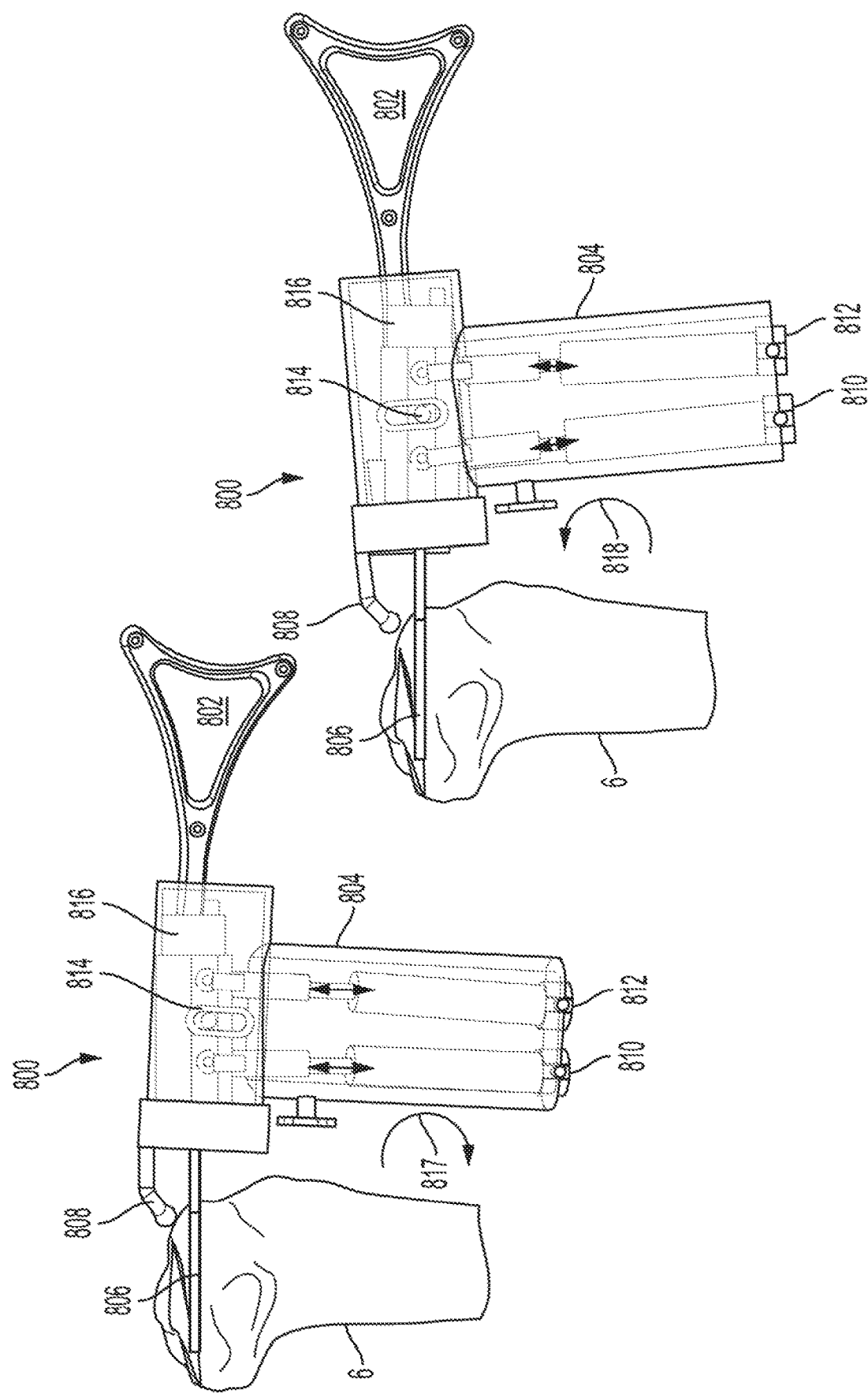
FIG. 9 is a pair of lateral cutaway views of a cutting tool compensating for tool body movement during a cutting operation on a patient bone, in accordance with some embodiments.

In some embodiments, the cutting guide 808 comprises an arm having a proximal end coupled to the tool body 804 and a distal contact end for contacting the patient bone 6 (as shown in greater detail in FIG. 9). In some embodiments, the cutting guide 808 extends from the tool body 804 in substantially the same direction as the tooltip 806 such that the cutting guide 808 may contact the surface of the patient bone 6 during bone resection.

In some embodiments, the cutting guide 808 is configured to contact an upper surface of the patient bone 6 during resection. For example, as shown in FIG. 8, the cutting guide 808 may be located above the tooltip 806 to contact an upper surface of the patient bone 6. A proximal portion of the arm may extend substantially parallel to the tooltip 806 and a distal portion of the arm may curve downward in the direction of the tooltip. However, in some embodiments, the cutting guide 808 may be substantially straight along its entire length.

Additional shapes and orientations for the cutting guide 808 are contemplated herein. In some embodiments, the proximal end of the cutting guide 808 may be coupled to another portion of the tool body 804 such as a portion to the left of the tooltip 806, a portion to the right of the tooltip, or a portion below the tooltip. For example, the proximal end of the cutting guide 808 may be coupled to a portion of the tool body 804 that houses the internal actuators, i.e., below the tooltip 806. Accordingly, the cutting guide 808 may be adequately sized to position the distal contact end above the tooltip 806 to contact the upper surface of the patient bone 6 during resection. The cutting guide 808 may include one or more curved portions that extend around and/or over the remainder of the tool body 804 in order to position the distal contact end of the cutting guide 808 above the tooltip 806.

The overall shape and position of the arm of the cutting guide 808 may be configured to provide adequate clearance between the cutting guide and the tooltip 806 to prevent interference with positioning of the tool 800 during resection. In some embodiments, the arm of the cutting guide 808 is adequately spaced from the tooltip 806 along the entire length of the cutting guide in order to prevent interference with positioning of tool 800, e.g., due to unintended contact of the cutting guide 808 with the patient bone 6.

In some embodiments, the distal contact end of the cutting guide 808 is configured to slide along the surface of the patient bone 6. In some embodiments, the distal contact end of the cutting guide 808 may be shaped to reduce resistance to sliding movement along the surface of the patient bone 6. For example, the distal contact end may comprise a sphere or a ball (as depicted in FIGS. 8-9) such that the distal contact end may slide along the surface of the patient bone. In some embodiments, the distal contact end may comprise a hemisphere or a portion of a sphere. Spherical shapes may be particular advantageous because rotation of the tool 800 (e.g., rotation about the pitch, yaw, and/or roll axes) will not substantially affect the contact with the patient bone 6. Therefore, the distal contact end may continue to slide along the surface of the patient bone 6 in substantially the same manner. In another embodiment, the distal contact end may comprise a substantially cylindrical shape. Additional or alternative smooth and/or rounded shapes may be implemented at the distal contact end as would be apparent to a person having an ordinary level of skill in the art.

FIG. 9 shows the operation of the tool 800 with active degrees of freedom as the forward pitch of the tool body 804 is changed. As shown in FIG. 9, the tooltip 806 may be rotated to cut in a direction coming out of the page. The surgeon places the cutting guide 808 in contact with the surface of the patient's condyle or tibial plateau at a location that allows the tooltip 806 to be manipulated in the predetermined cutting plane. The location of contact between the cutting guide 808 and the patient bone 6 also allows the surgeon to control the depth of the tooltip 806 so that the cut is made in the cutting plane at a depth that allows the tooltip to cut most of the depth of the patient bone, but leave enough bone past the tip to allow the surface of the bone 6 along which the cutting guide 808 rides to remain intact throughout the entire cutting process.

Within the tool body 804, linear actuators, such as 810 and 812, may provide, for example and without limitation, two degrees of freedom to manipulate the position and pitch of the tooltip 806 relative to the tool body. A sliding pin-and-slot 814 restricts the movement of the cutting tooltip 806 in the axial direction. The linear actuator devices 810 and 812 are described as linear actuators, but may include any suitable device that provides contraction and extension along an axis. In some embodiments, linear actuator devices may include any combination of linear motors, piezoelectric motors, pneumatic or hydraulic actuators, and gear motors with lead screws attached to the output shaft. Actuator devices, such as 810 and 812, can be mounted with pins to a motor housing 816 to allow the actuator devices to push or pull the motor housing without being rigidly coupled. The axis of the motor housing 816 may be parallel to the axis of the cutting tooltip 806. A motor within the motor housing 816 rotates the tooltip 806 at an angular velocity suitable to provide a cutting action in a direction transverse to that axis.

In one example, a surgeon's hand holds a portion of the tool body 804 below the motor housing 816 and deviates his hand position towards a patient bone 6 causing the tool body to move in a first direction 817. A processor controlling the linear actuators 810 and 812 may adjust the extension of the actuators to move the tool body 804 to compensate for the motion and direction 817 in which the tool 800 is moved. In another example, a surgeon's hand moves away from the patient bone 6 with a slight deviation. Such movement may cause the tool body 804 to move in a second direction 818. The processor controlling the linear actuators 810 and 812 may adjust the extension of the actuators to compensate for such movement by keeping the axis of the motor housing 816 and the tooltip 806 consistent with the cutting plane. For example, actuator 812 may contract more than actuator 810 (which may need to extend) to compensate.

Figure 10:
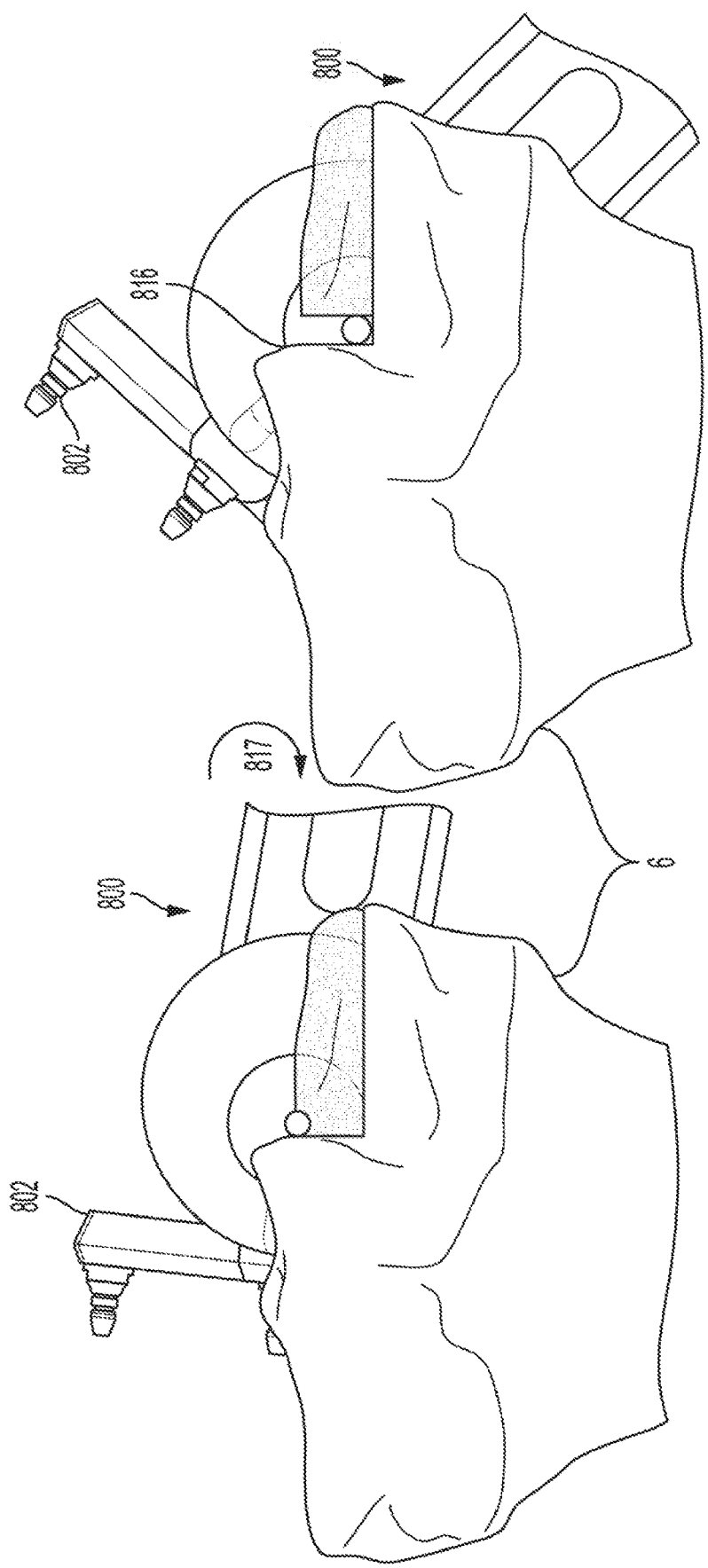
FIG. 10 is a pair of side views of a cutting tool performing a vertical cutting operation on a patient bone, in accordance with some embodiments.
Figure 11:
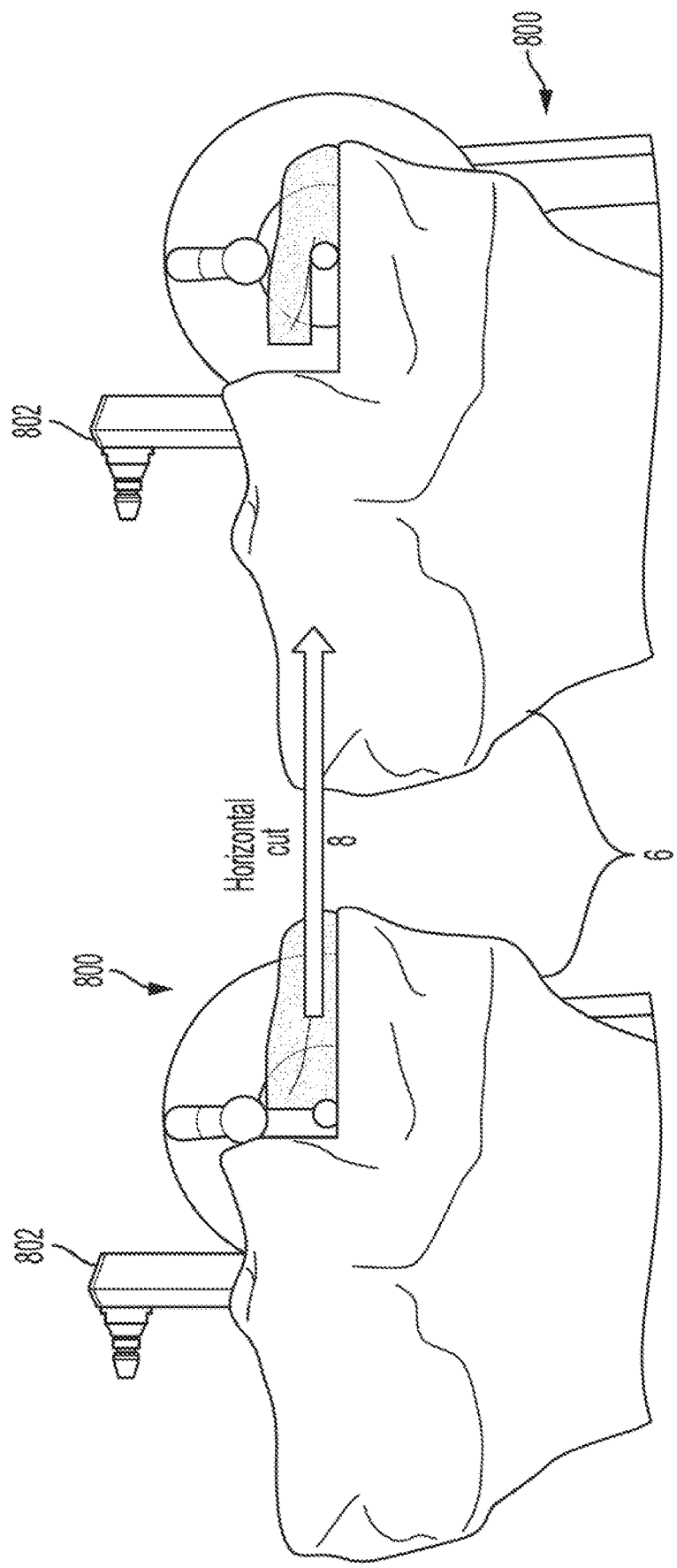
FIG. 11 is a pair of side views of a cutting tool performing a horizontal cutting operation on a patient bone, in accordance with some embodiments.

FIGS. 10 and 11 illustrates that a tool 800 having only two degrees of freedom can effectively achieve orthogonal cuts. This can be accomplished using a rotational movement of the tool body 804 during the first vertical cut and then holding the tool body in a vertical position during a horizontal cut. In this example, the tibial plateau is to be partially resected using two orthogonal cuts. The workflow uses the vertical cut as the initial cut followed by a cut in the horizontal cut plane. Because the tool only has two degrees of freedom, in this example, (allowing the processor to make adjustments in the vertical plane that is defined by the sheet in FIG. 9), the tool should be rotated such that the axis of the actuators are somewhat horizontal (e.g., within 40 degrees of being horizontal). Because the cut plane is perpendicular to the axis of the cutting tip, these degrees of freedom allow the vertical cutting plane to be generally perpendicular to the plane of the tool that defines the degrees of freedom. When the cutting plane is generally perpendicular to the axis of the actuators, the degrees of freedom give the processor the most control of the cutting tip. However, because the orientation of the cutting tip within that cutting plane generally does not matter (except near boundaries), the processor can still achieve control of the cutting tip to keep it within the cutting plane, even when the tool body is rotated such that the actuators are substantially deviated from being perpendicular to the direction of travel of the cutting tip (e.g., the bottom of the tool body can be substantially rotated in or out of the page up to 40+ degrees in FIG. 9 and still allow for the actuators to keep the cutting tip in the cutting plane). This is illustrated in FIG. 10.

To make the vertical cut, the operator places cutting guide 808 in contact with the head of the tibial plateau and holds of the tool roughly perpendicular to the long axis of the bone 6. Once the operator activates the cutting tip and engages the patient bone to make the vertical cut, the tool is pushed down and rotated. Because the cutting guide 808 is engaging the top of the tibial plateau, the vertical cut is not possible without rotation in this example. However, because the goal of the processor is to maintain the axis of the cutting tip within the vertical plane, and not necessarily hold the axis of the cutting tip perfectly horizontal, the cutting tip can be maintained in the vertical virtual cut plane even through this rotation with two degrees of freedom. In addition, the processor can control the speed of the cutting tool to prevent the end or any portion of the cutting tip from cutting past the second, horizontal cut plane. Furthermore, because the tool is rotated by the operator as the cut proceeds downward, the tool should be closer to vertical once the cutting tip nears the horizontal virtual cutting plane. This ensures that the degrees of freedom can be used to prevent the cutting tip from crossing that virtual boundary.

In some embodiments, during the vertical cut as the angle of the tool body is rotated towards the vertical position, the processor can intentionally deviate the cut from the vertical cut plane into the resected area, requiring later cleanup near the boundary between the vertical and horizontal cut plans. This cleanup can be done manually using rasps or osteotomes, as is conventionally done during surgery. This can be useful because as the tool becomes more vertical, the degrees of freedom are more limited in their ability to maintain the tooltip in the vertical cut plane. In some embodiments, the tooltip spin rate can be reduced by the processor as the tool moves into a more vertical position during this vertical cut to limit the damage that might occur while the degrees of freedom have less impact on keeping the cut coincident with the vertical virtual cut plane. In some embodiments, the operator intentionally does not rotate the cutting tool beyond a certain angle, such as 45 degrees, as shown in FIG. 10 during this vertical cut. This can limit the depth of the vertical cut due to the cutting guide, but ensures that the degrees of freedom have sufficient control over the cutting tip relative to the vertical cutting plane to avoid cutting outside the resection area, crossing either virtual cut plane.

In some embodiments, fiducial markers can be less effective as they are rotated away from the vertical position. As shown in FIG. 10, as the tool is rotated, the fiducial marker array 802 becomes less vertical and, beyond a certain angle, the fiducial marks, with some camera systems, may be less effective. Therefore, it may be undesirable to rotate the tool beyond a certain angle relative to any tracking cameras used in the surgical theater. As shown in FIG. 11, in some embodiments, the fiducial marker array 802 can be rotated manually before starting the horizontal cut. Encoders or user input may inform a processor of the rotation angle of the array, and the tracking system can account for the change in position of the fiducial marker array 802 relative to the tool body and cutting tip due to known tool geometry. In some embodiments, a multifaceted fiducial marker array 802 can be used that is three-dimensional, rather than a two-dimensional plane. This can allow the tool to operate in various orientations without repositioning the fiducial marker array 802. In some embodiments, the cutting guide 808 can also be rotated or removed by an operator to give more flexibility in the types of cuts possible.

Further, while the fiducial marker array 802 is described as being coupled to the tool body 804, the fiducial marker array 802 may be arranged in a variety of manners upon the tool 800. In some embodiments, the fiducial marker array 802 may be coupled to the motor housing 816 or a support thereon as depicted in FIG. 9 and may facilitate optical tracking of the position and location of the tool 800 and/or the tooltip 806 based on a known geometry between the tool body 804, the tooltip 806, and/or the motor housing 816. Reducing the number of components in the kinematic chain between the fiducial marker array 802 and the tooltip 806 in this manner may result in a reduced amount of error in the calculated position of the tooltip. Additional arrangements and orientations with respect to the tool 800 are contemplated herein as would be apparent to a person having an ordinary level of skill in the art.

In FIG. 11, the operator has completed the vertical cut and now rotates the tool body into a substantially vertical position. This allows the cutting guide to be substantially above the cutting tip and allows the cutting guide 808 to travel along the tibial plateau during the horizontal cut, providing a stable base for the operator's hand or robotic arm. During this cut, the tool is maintained in a substantially vertical position, ideally not changing the vertical orientation of the tool as it travels horizontally along the cut plane, within the operator's ability. Angular and vertical positional changes due to deviation in the motion of the surgeon's hand or robotic arm can be accounted for using the degrees of freedom under processor control. This ensures that as the operator moves the tool body the cutting tip travels in substantially the same plane as the virtual horizontal cut plane. The degrees of freedom compensate primarily for pitch and vertical position of the tooltip. Yaw is generally not compensated for, but does not affect the ability of the tooltip to stay within the horizontal cutting plane. It is not critical that the cutting tip remain parallel to the surface of the vertical cut during horizontal cut, except near the boundary of these two planes. Roll of the cutting tool can also be compensated for to the extent it affects the ability of the tooltip to stay within the cutting plane, but roll generally does not affect the ability of the rotary cutting tip to perform the cut due to the rotational nature of the cutting tool.

Figure 12:
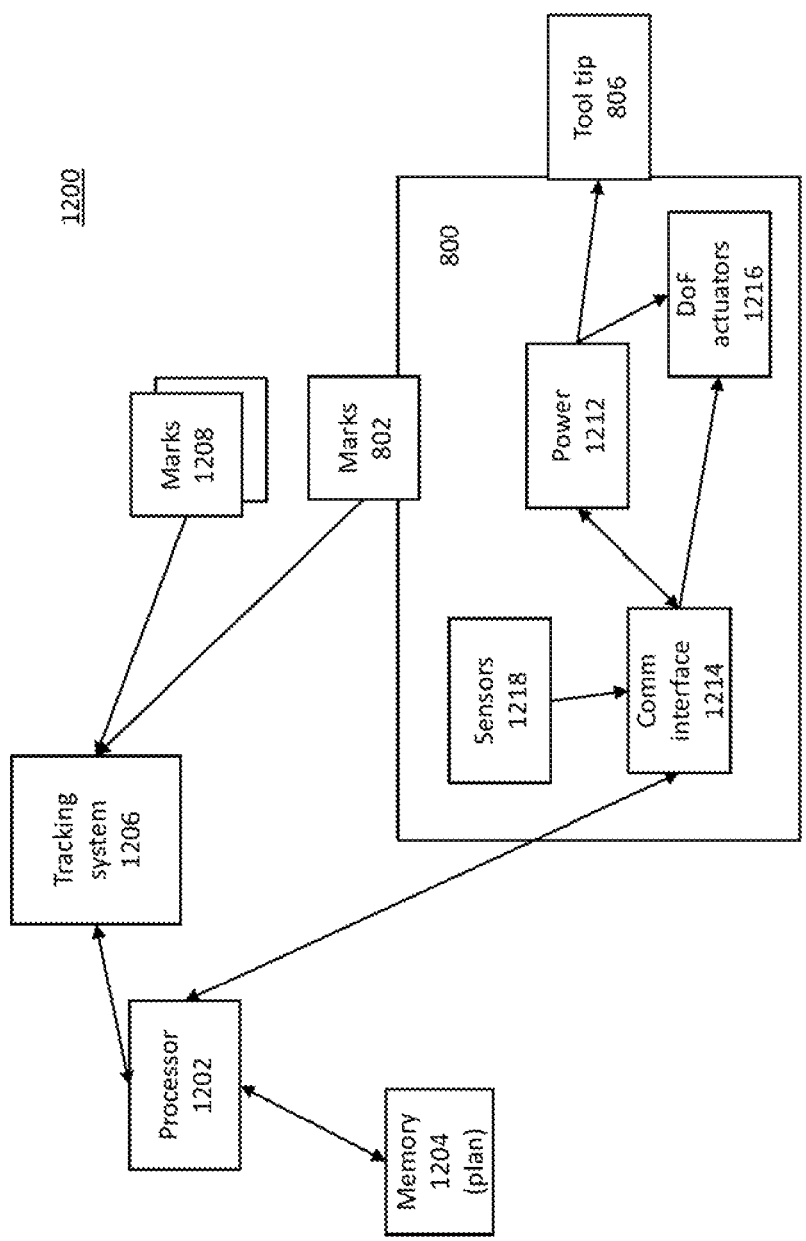
FIG. 12 is a system diagram of a surgical system utilizing a cutting tool, in accordance with some embodiments.

FIG. 12 is a top-level system diagram of a surgical system utilizing the multi-degree of freedom tool described herein. The system 1200 includes a processor 1202 that controls the operation of the degrees of freedom and the rotary motor of the tool. The processor 1202 controls the surgical tool in accordance with a surgical plan that can be stored in a non-transitory memory device 1204. The surgical plan can be a preoperative plan created prior to commencement of the surgery based on surgeon input and medical imaging, such as MRIs, CAT scans, x-rays, ultrasounds, etc. In some embodiments, the surgical plan can be updated or modified or created intraoperatively based on surgeon input. For example, ultrasound or x-ray information obtained or generated during surgery can be used to create or modify a surgical plan. Similarly, a surgeon can modify the surgical plan based on what she sees during surgery. For example, once a patient's anatomy is registered with a robotic tracking system, the surgeon may then interact with a model of the patient's anatomy on a user interface to create or update the surgical plan based on the surgeon's expertise and information learned by interacting with the patient anatomy. This can include moving patient joints and detecting resistances or strains or by determining the extent of damage once a patient's soft tissue is exposed. This can be useful for partial or total hip and knee arthroplasty, as well as any other joint surgery. In some embodiments, the processor 1202 automatically updates the surgical plan based on observed/imaged/recorded anatomical features or geometry and a model of the geometry of the prosthetic being implanted.

The processor 1202 is also in communication with a tracking system that utilizes any suitable tracking means to register and track patient anatomy (e.g. bones or soft tissue) and any relevant surgical tools, such as cutting tools, robotic arms, or surgical personnel. In this example, an optical tracking system is used. The tracking system 1206 can include one or more optical or IR cameras that record images of the surgical theater, which may include fiducial markers that have been registered to salient features of tools or anatomy. The tracking system 1206 processes the images to create a three-dimensional model of the relevant features of the environment. In the example of an optical tracking system, within the surgical theater a plurality of fiducial marks 1208 can be affixed to tools and patient anatomy; known geometry or input from surgery personnel can assist the image tracking system 1206 with determining the position and orientation of these marks or leads to relevant features, such as bone surfaces and the orientation or important geometry of tools being used by personnel.

The processor 1202 utilizes information gleaned from the tracking system 1206 to control the tool 800. The tool 800 can include an array or 3-dimensional group of fiducial markers 802 to allow the tracking system 1206 to model the orientation and position of the tool relative to the environment and communicate this information to the processor 1202. The processor 1202 communicates with the tool 800 via a communication interface 1214. The communication interface 1214 may communicate with the processor 1202 wirelessly or through a hardwired connection. In some embodiments, a hardwired connection provides a convenient and reliable means to send control and sensor information between the processor 1202 and the tool 800, particularly in embodiments in which the tool requires a power source. In some embodiments, the tool 800 may be a wireless battery-powered device and communication can occur wirelessly, such as via Wi-Fi, Bluetooth, or any other suitable wireless communication protocol. The communication interface 1214 receives power from a power source 1212. The power source 1212 can include a battery or an AC or DC connection to a central power source of the system 1200. The communication interface 1214 can send control signals responsive to the processor 1202 to the degree of freedom (DoF) controllers 1216 that control the linear actuators 810 and 812. Communication between the fiducial marker array 802, the image tracking system 1206, the processor 1202, the communication interface 1214, and the DoF controllers 1216 allows the processor to determine the position of the tool body 804 with respect to the patient's anatomy and to send control signals to actuators within the tool to compensate for deviations in position and orientation to ensure the tooltip 806 travels along the virtual cutting plane during a cutting operation.

In some embodiments, the communication interface may be used to control the power source 1212 and selectively send current to a motor that causes the tooltip 806 to rotate. In such embodiments, the speed of the rotary tool may be controlled by the processor 1202. In such embodiments, the processor 1202 may stop the rotary action of the tooltip 806 when the tooltip is in danger of intersecting another virtual cut plane or of leaving a prescribed cutting area. Similarly, the processor 1202 may selectively initiate a cutting operation in such embodiments.

In some embodiments, one or more sensors 1218 may provide additional information to the processor 1202 regarding the state of the cutting tool 800. For example, the one or more sensors 1218 may include a switch that allows a surgeon to selectively instruct the processor 1202 to start the cutting operation. The processor 1202 may control the DoF controllers 1216 and selectively provide power to the cutting tooltip 806 to perform the cutting operation in accordance with the surgical plan and the real time location of the cutting tip. The one or more sensors 1218 can also include one or more encoders that provide information about the state of the actuators 810 and 812 and the speed of the cutting tooltip 806 to the processor 1202.

Figure 13:
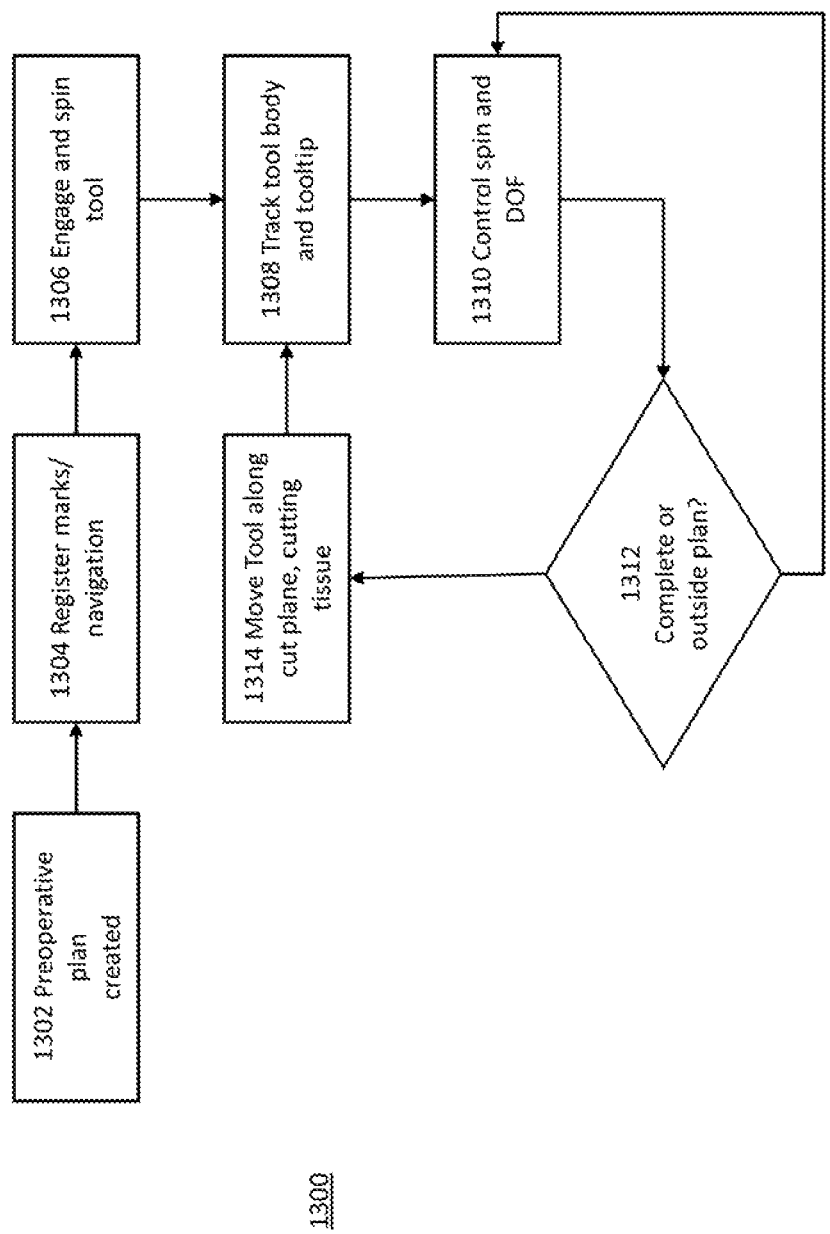
FIG. 13 is a flowchart of the exemplary operation of a surgical system utilizing a cutting tool, in accordance with some embodiments.

FIG. 13 is a flow chart of an exemplary method 1300 for using a surgical rotary tool, in accordance with some embodiments. At step 1302, a surgical plan is created. This can include a plan generated automatically using a machine learning algorithm or through human interaction based on 3D (MRI, CT scan, 3D ultrasound) or 2D (x-ray or ultrasound) medical imaging. The surgical plan can include a model of one or more implants and the cutting planes to be used relative to the geometry of the bone tissue to ensure proper functioning of arthroplasty implants, such as partial or total knee or hip replacement hardware.

At step 1304, during the surgery, the position tracking system is calibrated and prepared. This can include mounting fiducial marker arrays to patient bones and registering the location of these fiducial marker arrays relative to bone joint surfaces, such as by "painting" a joint surface using a stylus having a fiducial marker array once the fiducial marker arrays of the patient bones are registered to the tracking system. This can also include using a robotic arm to interact with patient bone surfaces to register those surfaces relative to the robotic arm geometry to create a model of patient anatomy relative to known positions of features of the robotic arm.

Once the environment is prepared for tracking, at step 1306, the rotary tool is placed in contact with patient bone tissue and resection can begin. Resection begins by placing the tool cutting guide 808 in contact with some known surface of patient bone tissue and rotating the rotary cutting tooltip as it engages the patient tissue.

At step 1308, the position of the tool body and the tooltip are tracked relative to the patient's anatomy. This can include tracking the position of a robotic arm of known geometry that holds the tool body of known geometry and identifying the location of the cutting tip based on the state of linear actuators that control the position and orientation of the cutting tip. This can also include optically tracking a fiducial marker array fixed to the tool body and using a model of the geometry of the fiducial marker array relative to the tool body and a model of the actuators and by extension location of the tooltip relative to the tool body. In some embodiments, the tracking system has means of optically or directly tracking the orientation of the tooltip.

At step 1310, the processor, in response to tracking the body and tooltip relative to the patient anatomy, controls the rotational speed and degrees of freedom of the tool. This, in turn, controls the cutting location of the tooltip relative to the patient anatomy to compensate for the position and orientation of the tool body. Speed can be controlled to make the cut, stop a cut, slow down a cut, etc. In some embodiments, more than two degrees of freedom can be used to add additional control to a tooltip (i.e., other than ensuring that the tooltip is within a plane that is roughly perpendicular to the main axis of the tool body). For example, the depth of the distal end of the tooltip can be controlled relative to the tool body to increase or decrease the depth of the cut, lateral degrees of freedom can be used to adjust the relative angle of the tooltip within the plane of the cut to assist the surgeon with precise motion within the cutting plane, or the like.

At step 1312, the processor determines whether the cut is complete or whether the tooltip is deviating from the surgical plan such that it is about to cut into tissue beyond the length of the planned cut (e.g. past the intersection of vertical and horizontal cutting plans). If so, the processor may reduce the rotational speed of the shaft of the rotary tool and repeat step 1310. If not, the process may continue as the surgeon or the robotic arm moves the tool along the cutting plane at step 1314. This may result in cutting the bone tissue in accordance with the surgical plan in the virtual cutting plane. This cycle may then revert to step 1308, repeatedly tracking the tooltip location and compensating for the position and angle of the tool body and determining whether or not the cut is complete as the surgeon moves the tool.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

While the devices, systems, and methods are particularly described for performing tibial cuts, the devices, systems, and methods may also be utilized for performing femoral cuts. For example, one or more distal femur cuts, anterior cuts, posterior cuts, and/or chamfer cuts may be performed by the devices, systems, and methods described herein.

While the tool body 804 is depicted as enclosing the linear actuators 810/812 and the motor housing 816, in some embodiments one or more components may be external to the tool body 804. For example, the motor housing 816 may be external to the tool body 804. In some embodiments, the tool body 804 encloses the linear actuators 810/812 and is sealed off below the motor housing 816. For example, a flexible material may be used to seal the tool body 804 around the linear actuators 810/812 at an interface with the motor housing 816. Additional configurations of the tool body 804 are contemplated as would be apparent to a person having an ordinary level of skill in the art.

In some embodiments, the tool body 804 may further comprise a front guard to prevent the tool 800 from being advanced towards the patient bone 6 beyond a predetermined distance. For example, the front guard may extend from the tool body 804 in substantially the same direction as the tooltip 806 (as shown in FIG. 9) to maintain the tool 800 at least at a predetermined distance from the patient bone 6, thereby preventing the tooltip 806 from cutting beyond a planned depth and/or damaging other portions of the patient anatomy.

In some embodiments, the cutting guide 808 is adjustable to change an offset distance between the cutting guide and the tooltip 806. For example, the offset distance may be adjusted to roughly match a distance of the virtual cutting plane from the surface of the patient bone 6. In some cases, adjustment of the cutting guide 808 may be necessary to reach the virtual cutting plane with the tooltip 806 because the linear actuators 810/812 may have a limited ability to vertically reposition the tooltip.

In some embodiments, a plurality of removable cutting guides 808 may be provided. In some embodiments, each removable cutting guide 808 is configured for a different offset distance from the tooltip 806, and a surgeon may select a cutting guide 808 based on the required offset distance. In some embodiments, a proximal end of the cutting guide 808 may be threaded and configured to mate with a bore on the tool body 804 having corresponding threads to secure the cutting guide to the tool body. In some embodiments, the cutting guide 808 may be configured to mate with a bore on the tool body 804 by friction or interference fit. Additional manners of mating the cutting guide 808 with the tool body 804 are contemplated herein as would be apparent to a person having an ordinary level of skill in the art. In some embodiments, the cutting guide 808 may include indicia associated with the offset distance that may be input to the processor. For example, the indicia may indicate the offset distance as a measurement and/or an indexed number or setting that corresponds to the known offset distance of each removable cutting guide 808. The processor may determine the offset distance based on the indicia and utilize the offset distance for controlling the tooltip 806 as further described herein.

In some embodiments, the cutting guide 808 forms an adjustable joint with the tool body 804 for changing the offset distance. For example, the cutting guide 808 may be threaded into the tool body 804 or otherwise axially rotatable (i.e., about a roll axis) with respect to the tool body. Accordingly, in embodiments in which the cutting guide 808 includes one or more curves or bends, rotation of the cutting guide may result in a change in the offset distance of the distal contact end of the cutting guide from the tooltip 806. Where a plurality of removable cutting guides 808 are provided as described herein, the adjustable joint may be utilized to make minor adjustments to the offset distance (i.e., fine tuning).

In some embodiments, the cutting guide 808 comprises an adjustable joint along the arm for changing the offset distance. For example, the adjustable joint may be a hirth joint formed with the tool body 804 or at a point along the arm of the cutting guide 808. Mating portions of the hirth joint may include interlocking teeth that are secured together by a screw or other fastener to lock the joint. In some embodiments, the offset distance may be changed by rotating a first mating portion with respect to a second mating portion about a pitch axis, thereby changing the pitch of the arm of the cutting guide 808 and rotating the distal contact end towards or away from the tooltip 806. When an adequate offset distance is achieved, the mating portions may be locked together by the screw. In some embodiments, the adjustable joint may include indicia associated with the offset distance that may be input to the processor as described herein. For example, the indicia may indicate the offset distance as a measurement and/or an indexed number or setting that corresponds to a known offset distance based on the position of the adjustable joint. The processor may determine the offset distance based on the indicia and utilize the offset distance for controlling the tooltip 806 as further described herein.

In some embodiments, the cutting guide 808 may be formed from a semi-rigid material. For example, the cutting guide 808 may be formed from a stiff wire. The semi-rigid material may be sufficiently flexible to be re-shaped under a relatively high force, e.g., forceful bending by a surgeon's hand, and sufficiently rigid to hold the shape against relatively low forces, e.g., routine contact forces during a resection.

In some embodiments, the distal contact end of the cutting guide 808 may comprise a low-friction surface or a low-friction coating thereon to reduce resistance to movement of the distal contact end along the surface of the patient bone 6.

The cutting guide 808 may be altered in various manners to increase a contact surface with the patient bone to improve stability of the tool 800. In some embodiments, a plurality of distal contact ends may be included on the cutting guide 808. For example, two or more spherical balls may extend from the cutting guide 808 (e.g., a fork-shaped cutting guide) to further stabilize the tool 800 and reduce rotation in an additional degree of freedom. In some embodiments, the distal contact end may be formed as a plate that is freely rotatable with respect to the tool body 804. For example, the spherical ball of the cutting guide 808 as shown in FIG. 9 may be received within a socket of a plate element to form a ball and socket joint. The plate element may serve as the distal contact end and rest on the surface of the patient bone 6 to provide greater stability to the tool 800.

In some embodiments, the tool rest or cutting guide 808 is provided separately from the tool body 804. In some embodiments, the cutting guide 808 is configured to be secured to the patient bone 6 or another portion of the patient anatomy such that the tool body 804 and tooltip 806 may contact the cutting guide 808 to rest thereon and stabilize the tool 800. For example, the cutting guide 808 may be a rigid element that may be secured to the patient anatomy and fixed with respect thereto. The cutting guide 808 may be secured to the patient anatomy by adjustable straps (e.g., one or more straps secured by hook and loop fasteners) or any other means of securement as would be known to a person having an ordinary level of skill in the art. In some embodiments, the cutting guide 808 includes a flat or substantially planar surface for receiving a portion of the tool body 804 or the tooltip 806. In some embodiments, the tool 800 may rest upon the cutting guide 808 and may be moved along the planar surface as the cut is completed, thereby providing additional stability to the tool 800 and/or relieving stress on the surgeon's hand during the resection. In some embodiments, the cutting guide 808 may comprise a low-friction surface or a low-friction coating thereon to reduce resistance to movement of the tool body 804 along the cutting guide.

In one example, the rigid element may be an L-shaped bracket or a U-shaped bracket that forms a ledge for resting and guiding the tool 800. The bracket may be strapped to the tibia to perform tibial cuts and/or to the femur to perform femoral cuts. The bracket may have sufficient depth to receive the tool 800 and to allow some movement of the tool 800 towards or away from the patient bone 6. In some embodiments, a patient-contacting face of the bracket comprises padding or foam to conform to the shape of the patient anatomy and reduce discomfort to the patient. In some embodiments, a horizontal surface of the bracket may be utilized to guide the tool 800 through the horizontal cut on the tibia. Similarly, a vertical surface of the bracket may be utilized to guide the tool 800 through the vertical cut on the tibia. In some embodiments, the bracket may also be used to guide the tool 800 through horizontal and/or vertical cuts on the femur in a similar manner. In some embodiments, the bracket may include a guard or backstop to prevent the tool 800 from being advanced towards the patient bone 6 beyond a predetermined distance. For example, the guard or backstop may maintain the tool 800 at least at a predetermined distance from the patient bone 6, thereby preventing the tooltip 806 from cutting beyond a planned depth and/or damaging other portions of the patient anatomy.

In some embodiments, the bracket may be used to guide the tool 800 through chamfer cuts on the femur. Because the chamfer cuts may be angled with respect to the longitudinal axis of the patient bone (e.g., approximately 45°), the bracket and/or the patient bone may be repositioned to provide an appropriately angled ledge for the tool 800. For example, the bracket may be strapped to the tibia and the knee joint may be flexed to position the femur at an appropriate angle with the bracket. In another example, the bracket (e.g., an L-shaped bracket) may be rotated 45° and strapped to the femur, thereby providing two surfaces angled at 45° from the longitudinal axis of the femur for guiding the chamfer cuts on opposing sides of the patient bone. In some embodiments, separate cutting guides 808 may be provided for the tibia and the femur. In some embodiments, the surgeon may select an advantageous order for performing various cuts of one or more bones to reduce repositioning of the cutting guide 808.

In some embodiments, the bracket may include an adjustable ledge. The adjustable ledge may allow for minor adjustments to the position of the ledge with respect to the cutting plane without uncoupling the bracket from the patient anatomy. In some embodiments, a U-shaped bracket may include a separate flat movable platform reversibly coupled to one or both of the vertical portions of the bracket. For example, the vertical portions may include a plurality of holes and/or an extended slot for receiving the platform and securing by a fastener at various heights on the U-shaped bracket. In some embodiments, the movable platform may also be configured to be positioned at an angle, e.g., for guiding chamfer cuts on a femur. In some embodiments, a movable platform may be provided on an L-shaped bracket with minor modifications.

Figure 14:
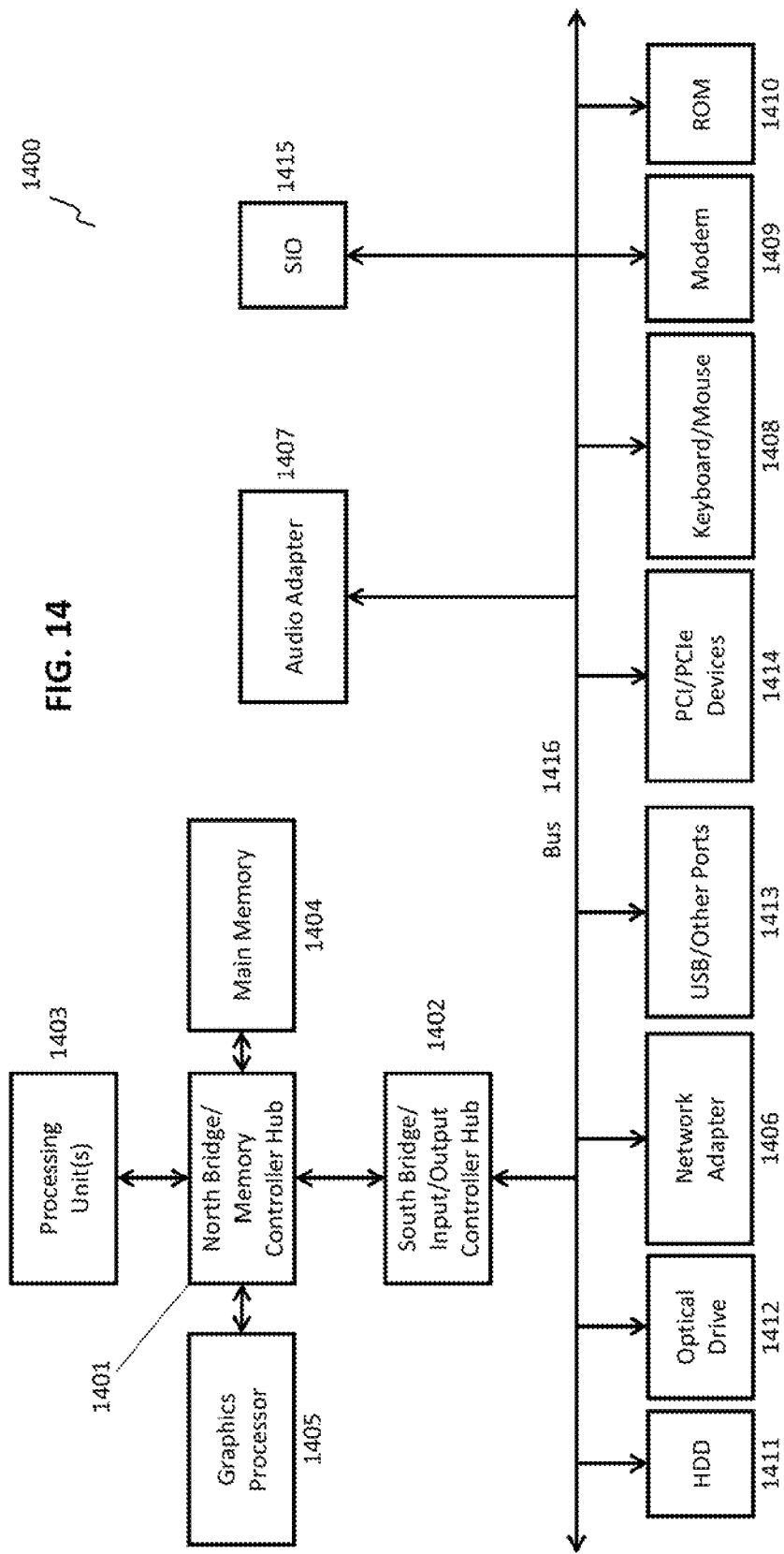
FIG. 14 depicts a block diagram of an example environment for operating a system for navigation and control of a computer-aided surgical navigation system according to an illustrative embodiment.

FIG. 14 is a block diagram of an example data processing system 1400 in which aspects of the illustrative embodiments are implemented. Data processing system 1400 is an example of a computer, such as a server or client, in which computer usable code or instructions implementing the process for illustrative embodiments of the present invention are located. In one embodiment, FIG. 14 may represent a server computing device.

In the depicted example, data processing system 1400 can employ a hub architecture including a north bridge and memory controller hub (NB/MCH) 1401 and south bridge and input/output (I/O) controller hub (SB/ICH) 1402. Processing unit 1403, main memory 1404, and graphics processor 1405 can be connected to the NB/MCH 1401. Graphics processor 1405 can be connected to the NB/MCH 1401 through, for example, an accelerated graphics port (AGP).

In the depicted example, a network adapter 1406 connects to the SB/ICH 1402. An audio adapter 1407, keyboard and mouse adapter 1408, modem 1409, read only memory (ROM) 1410, hard disk drive (HDD) 1411, optical drive (e.g., CD or DVD) 1412, universal serial bus (USB) ports and other communication ports 1413, and PCI/PCIe devices 1414 may connect to the SB/ICH 1402 through bus system 1416. PCI/PCIe devices 1414 may include Ethernet adapters, add-in cards, and PC cards for notebook computers. ROM 1410 may be, for example, a flash basic input/output system (BIOS). The HDD 1411 and optical drive 1412 can use an integrated drive electronics (IDE) or serial advanced technology attachment (SATA) interface. A super I/O (SIO) device 1415 can be connected to the SB/ICH 1402.

An operating system can run on processing unit 1403. The operating system can coordinate and provide control of various components within the data processing system 1400. As a client, the operating system can be a commercially available operating system. An object-oriented programming system, such as the Java™ programming system, may run in conjunction with the operating system and provide calls to the operating system from the object-oriented programs or applications executing on the data processing system 1400. As a server, the data processing system 1400 can be an IBM® eServer™ System p® running the Advanced Interactive Executive operating system or the Linux operating system. The data processing system 1400 can be a symmetric multiprocessor (SMP) system that can include a plurality of processors in the processing unit 1403. Alternatively, a single processor system may be employed.

Instructions for the operating system, the object-oriented programming system, and applications or programs are located on storage devices, such as the HDD 1411, and are loaded into the main memory 1404 for execution by the processing unit 1403. The processes for embodiments described herein can be performed by the processing unit 1403 using computer usable program code, which can be located in a memory such as, for example, main memory 1404, ROM 1410, or in one or more peripheral devices.

A bus system 1416 can be comprised of one or more busses. The bus system 1416 can be implemented using any type of communication fabric or architecture that can provide for a transfer of data between different components or devices attached to the fabric or architecture. A communication unit such as the modem 1409 or the network adapter 1406 can include one or more devices that can be used to transmit and receive data.

Those of ordinary skill in the art will appreciate that the hardware depicted in FIG. 14 may vary depending on the implementation. Other internal hardware or peripheral devices, such as flash memory, equivalent non-volatile memory, or optical disk drives may be used in addition to or in place of the hardware depicted. Moreover, the data processing system 1400 can take the form of any of a number of different data processing systems, including but not limited to, client computing devices, server computing devices, tablet computers, laptop computers, telephone or other communication devices, personal digital assistants, and the like. Essentially, data processing system 1400 can be any known or later developed data processing system without architectural limitation.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for resecting a bone of a patient, the system comprising:
   a rotary tool having:
      a tool body,
      a tracking array affixed to the tool body, the tracking array comprising three or more fiducial markers,
      a powered rotary cutting tip comprising a longitudinal axis, wherein the powered rotary cutting tip is affixed to the tool body and rotatable about the longitudinal axis by a motor to resect the bone,
      first and second linear actuators configured to adjust one or more of a vertical position and a pitch position of the powered rotary cutting tip with respect to the tool body, and
      a tool rest extending from the tool body configured to maintain contact with the bone at a portion that is intended to be resected and removed as the tool body is moved during a portion of a surgical procedure;
   a surgical tracking device configured to identify a position of each of the three or more fiducial markers with respect to the bone; and
   a processor configured to cause the system to:
      receive a surgical plan comprising at least one virtual cutting plane on the bone,
      receive the position of the three or more fiducial markers from the surgical tracking device,
      determine, based on the position of the three or more fiducial markers, a real-time pose of the cutting tip with respect to the at least one virtual cutting plane, and
      control the first and second linear actuators, based on the real-time pose, to adjust one or more of the vertical position and the pitch position of the rotary cutting tip with respect to the tool body to maintain the powered rotary cutting tip on the at least one virtual cutting plane.

2. The system of claim 1, wherein the powered rotary cutting tip has a fixed horizontal position and a fixed axial position with respect to the tool body.

3. The system of claim 1, wherein the powered rotary cutting tip has a fixed yaw position with respect to the tool body.

4. The system of claim 1, wherein the processor is configured to prevent the powered rotary cutting tip from cutting across the at least one virtual cutting plane.

5. The system of claim 1, wherein the at least one virtual cutting plane comprises a vertical cutting plane and a horizontal cutting plane, and wherein the tool rest is configured separate from the portion of the bone being resected during a second portion of the surgical procedure comprising a resection along the vertical cutting plane.

6. The system of claim 5, wherein the processor is further configured to:
   maintain the longitudinal axis of the powered rotary cutting tip on the vertical cutting plane when a movement axis of the first and second linear actuators is substantially orthogonal to the vertical cutting plane; and
   maintain the longitudinal axis of the powered rotary cutting tip on the horizontal cutting plane when the movement axis of the first and second linear actuators is substantially orthogonal to the horizontal cutting plane.

7. The system of claim 5, wherein the tool rest is further configured to:
   pivot about a fixed point on a contact surface with the bone during movement of the powered rotary cutting tip along the vertical cutting plane; and
   move along the contact surface of the bone during movement of the powered rotary cutting tip along the horizontal cutting plane.

8. The system of claim 1, wherein the processor is further configured to control a speed of rotation of the powered rotary cutting tip about the longitudinal axis to resect the bone.

9. The system of claim 8, wherein the processor is further configured to stop rotation of the powered rotary cutting tip when the rotary cutting tip intersects the at least one virtual cutting plane.

10. The system of claim 8, wherein the processor is further configured to stop rotation of the powered rotary cutting tip when the rotary cutting tip is moved outside of a prescribed cutting area.

11. The system of claim 1, wherein each of the first and second linear actuators comprises one or more of a linear motor, a piezoelectric motor, a pneumatic motor, a hydraulic motor, and a gear motor.

12. The system of claim 1, wherein the tool rest is rotatable with respect to the tool body.

13. The system of claim 1, wherein the processor is further configured to control a position of a robotic arm to which the rotary tool is affixed.

14. A rotary cutting tool for resecting a bone of a patient, the rotary cutting tool comprising:
   a tool body;
   a tracking array affixed to a tool body, the tracking array comprising one or more fiducial markers configured to be tracked by a surgical tracking system;
   a powered rotary cutting tip comprising a longitudinal axis, wherein the powered rotary cutting tip is affixed to the tool body and rotatable about the longitudinal axis by a motor to resect the bone of the patient;
   first and second linear actuators configured to be actuated to adjust one or more of a vertical position and a pitch position of the powered rotary cutting tip with respect to the tool body to maintain the powered rotary cutting tip on at least one virtual cutting plane; and
   a tool rest extending from the tool body and configured to maintain contact with the bone at a portion that is intended to be resected and removed as the tool body is moved during a portion of a surgical procedure.

15. The rotary tool of claim 14, wherein the powered rotary cutting tip has a fixed horizontal position and a fixed axial position with respect to the tool body.

16. The rotary tool of claim 14, wherein the powered rotary cutting tip has a fixed yaw position with respect to the tool body.

17. The rotary tool of claim 14, wherein each of the first and second linear actuators comprises one or more of a linear motor, a piezoelectric motor, a pneumatic motor, a hydraulic motor, and a gear motor.

18. The rotary tool of claim 14, wherein the tool rest is rotatable with respect to the tool body.

19. The rotary tool of claim 14, wherein the tool rest is further configured to:
 pivot about a fixed point on a contact surface with the bone during movement of the powered rotary cutting tip along a vertical cutting plane; and
 move along the contact surface of the bone during movement of the powered rotary cutting tip along a horizontal cutting plane.

20. A system for resecting a bone of a patient, the system comprising:
 a rotary tool having:
  a tool body,
  a tracking array affixed to the tool body, the tracking array comprising three or more fiducial markers,
  a powered rotary cutting tip comprising a longitudinal axis, wherein the powered rotary cutting tip is affixed to the tool body and rotatable about the longitudinal axis by a motor to resect the bone,
  first and second linear actuators configured to adjust one or more of a vertical position and a pitch position of the powered rotary cutting tip with respect to the tool body, and
  a tool rest extending from the tool body and configured to maintain contact with a portion of the bone at a portion that is intended to be being resected and removed as the tool body is moved to resect the bone during a portion of a surgical procedure;
 a surgical tracking device configured to identify a position of each of the three or more fiducial markers with respect to the bone;
 a processor; and
 a non-transitory, computer-readable medium storing instructions that, when executed, cause the system to:
  receive a surgical plan comprising at least one virtual cutting plane on the bone,
  receive the position of the three or more fiducial markers from the surgical tracking device,
  determine, based on the position of the three or more fiducial markers, a real-time pose of the cutting tip with respect to the at least one virtual cutting plane, and
  control the first and second linear actuators, based on the real-time pose, to adjust one or more of the vertical position and the pitch position of the rotary cutting tip with respect to the tool body to maintain the powered rotary cutting tip on the at least one virtual cutting plane.

\* \* \* \* \*